(12) United States Patent
Yan et al.

(10) Patent No.: US 7,842,836 B2
(45) Date of Patent: Nov. 30, 2010

(54) N-ARYL-N'ALKYL SULFAMIDES AS MEK INHIBITORS

(75) Inventors: Shunqi Yan, Irvine, CA (US); Jean-Michel Vernier, Laguna Niguel, CA (US); Zhi Hong, Irvine, CA (US)

(73) Assignee: Ardea Biosciences, Costa Mesa, CA (US)

( * ) Notice: Subject to any disclaimer, the term of this patent is extended or adjusted under 35 U.S.C. 154(b) by 0 days.

(21) Appl. No.: 11/734,234

(22) Filed: Apr. 11, 2007

(65) Prior Publication Data

US 2007/0238710 A1    Oct. 11, 2007

Related U.S. Application Data

(60) Provisional application No. 60/791,290, filed on Apr. 11, 2006.

(51) Int. Cl.
*C07C 331/00* (2006.01)
*A61K 31/10* (2006.01)

(52) U.S. Cl. .......................................... 564/79; 514/709
(58) Field of Classification Search ................... 564/79; 514/709
See application file for complete search history.

(56) References Cited

U.S. PATENT DOCUMENTS

| 5,596,008 | A | 1/1997 | Lee et al. |
|---|---|---|---|
| 5,861,510 | A | 1/1999 | Piscopio et al. |
| 5,863,949 | A | 1/1999 | Robinson et al. |
| 6,235,764 | B1 | 5/2001 | Larson et al. |
| 6,495,582 | B1 | 12/2002 | Hale et al. |
| 6,511,993 | B1 | 1/2003 | Dack et al. |
| 6,548,526 | B2 | 4/2003 | Larson et al. |
| 6,649,640 | B2 | 11/2003 | Hale et al. |
| 6,989,451 | B2 | 1/2006 | Zhang et al. |
| 2003/0149015 | A1 | 8/2003 | Barrett et al. |
| 2004/0029898 | A1 | 2/2004 | Boyle et al. |
| 2004/0039037 | A1 | 2/2004 | Zhang et al. |
| 2004/0152691 | A1 | 8/2004 | Lippa et al. |
| 2005/0143438 | A1 | 6/2005 | Wallace et al. |
| 2007/0244164 | A1 | 10/2007 | Yan et al. |
| 2008/0058340 | A1 | 3/2008 | Maderna et al. |

FOREIGN PATENT DOCUMENTS

| EP | 0239362 | A2 | 9/1987 |
|---|---|---|---|
| EP | 0606046 | A1 | 7/1994 |
| EP | 0780386 | A1 | 6/1997 |
| EP | 0818442 | A2 | 1/1999 |
| EP | 0931788 | A2 | 8/1999 |
| EP | 1004578 | A2 | 5/2000 |
| EP | 1181017 | A1 | 2/2002 |
| WO | WO 90-05719 | A1 | 5/1990 |
| WO | WO 96-27583 | A1 | 9/1996 |
| WO | WO 96-33172 | A1 | 10/1996 |
| WO | WO 98-03516 | A1 | 1/1998 |
| WO | WO 98-07697 | A1 | 2/1998 |
| WO | WO 98-30566 | A1 | 7/1998 |
| WO | WO 98-33768 | A1 | 8/1998 |
| WO | WO 98-34915 | A1 | 8/1998 |
| WO | WO 98-34918 | A1 | 8/1998 |
| WO | WO 99-07675 | A1 | 2/1999 |
| WO | WO 99-29667 | A1 | 6/1999 |
| WO | WO 99-52889 | A1 | 10/1999 |
| WO | WO 99-52910 | A1 | 10/1999 |
| WO | WO 03-043985 | A1 | 5/2003 |

OTHER PUBLICATIONS

Silverman, R. B. (The Org. Chem. of Drug Design and Drug Action, Academic Press, Inc.: San Diego, 1992, pp. 4-51).*
Shibata et al. (CAPLUS abstract of WO 2004/083167).*
Kubinyi (3D QSAR in Drug Design: Ligand-Protein Interactions and Molecular Similarity, vol. 2-3, Springer, 1998, 800 pages).*
Byrn et al., Pharm. Res., v. 12, n. 7, p. 945-54, 1995.*
Khire et al., Bioorganic & Medicinal Chemistry Letters 14 (2004) 783-786.*
Zhang et at., Bioorganic & Medicinal Chemistry Letters 10 (2000) 2825-2828.*
English and Cobb (Trends in Pharmacological Sciences vol. 23 No. 1 Jan. 2002, p. 40-45).*
Berge et al., "Pharmaceutical salts," J. Pharm. Sci. 66(1): 1-19, 1977.
Buchwald et al., "Long-term, continuous intravenous heparin administration by an implantable infusion pump in ambulatory patients with recurrent venous thrombosis," Surgery 88(4): 507-16, 1980.
Bundgaard, H. Chapter 5: Design and application of prodrugs. A Textbook of Drug Design and Development. Krosgaard-Larsen, et al., eds., pp. 113-191, 1991.
Bundgaard, H., "Means to enhance penetration: Prodrugs as a means to improve the delivery of peptide drugs," Advanced Drug Delivery Reviews 8: 1-38, 1992.
Fedorak et al., "A novel colon-specific steroid prodrug enhances sodium chloride absorption in rat colitis," Am J Physiol 269(2 Pt 1): G210-8, 1995.
Fleisher et al., "Improved oral drug delivery: solubility limitations overcome by the use of prodrugs," Advanced Drug Delivery Reviews 19(2): 115-30, 1996.
Furniss et al., ed., Vogel's Textbook of Practical Organic Chemistry, 5th Ed. Suppl. (Longman Scientific and Technical Ltd, Essex, UK) pp. 809-816, 1991.
Goodson, J. Dental applications. Medical Applications of Controlled Release, vol. 2, Applications and Evaluations. Langer, et al., eds. (CRC Press, Boca Raton, FL) pp. 115-138, 1984.
Heller, A., "Electrical wiring of redox enzymes," Acc Chem Res 23(5): 128-34, 1990.
Hochhaus et al. A selective HPLC/RIA for dexamethasone and its prodrug dexamethasone-21-sulphobenzoate sodium in biological fluids. Biomed Chromatogr. 1992; 6(6): 1992.

(Continued)

*Primary Examiner*—Robert Havlin
(74) *Attorney, Agent, or Firm*—Millen, White, Zelano & Branigan, P.C.

(57) ABSTRACT

This invention concerns N-(ortho phenylaminoaryl), N'-alkyl sulfamides which are inhibitors of MEK and are useful in the treatment of cancer and other hyperproliferative diseases.

17 Claims, No Drawings

OTHER PUBLICATIONS

Langer, R., "New methods of drug delivery," Science 249(4976): 1527-33, 1990.

Larsen, et al., "Prodrug forms for the sulfonamide group. I. Evaluation of N-acyl derivative, N-sulfonylamidines, N-sulfonylsulfilimines and sulfonylureas as possible prodrug derivatives," Int J Pharmaceutics 37(1-2): 87-95, 1987.

Larsen et al., "Prodrug forms for the sulfonamide group. II. Water-soluble amino acid derivatives of N-methylsulfonamides as possible prodrugs," Int J Pharmaceutics 47(1-3): 103-10, 1988.

McLeod et al., "A glucocorticoid prodrug facilitates normal mucosal function in rat colitis without adrenal suppression," Gastroenterology 106(2): 405-13, 1994.

Robinson et al., "Discovery of the hemifumarate and (alpha-L-alanyloxy)methyl ether as prodrugs of an antirheumatic oxindole: prodrugs for the enolic OH group," J Med Chem 39(1): 10-8, 1996.

Saudek et al., "A preliminary trial of the programmable implantable medication system for insulin delivery," N. Engl J Med 321(9): 574-9, 1989.

Saulnier et al., "An efficient method for the synthesis of guanidino prodrugs," Bioorganic & Medicinal Chemistry Letters 4(16): 1985-90, 1994.

Sefton, M., "Implantable pumps," Crit Rev Biomed Eng 14(3): 201-40, 1987.

Sinkula et al., "Rationale for design of biologically reversible drug derivatives: prodrugs," J Pharm Sci 64(2): 181-210, 1975.

Treat et al., "Liposome encapsulated doxorubicin: Preliminary results of phase I and phase II trials," Liposomes in the Therapy of Infectious Diseases and Cancer. Lopez-Bernstein, et al., eds. (Alan R. Liss, New York) pp. 353-365, 1989.

Varaprasad et al., "Discovery of 3-hydroxy-4-carboxyalkylamidino-5-arylamino-isothiazoles as potent MEK1 inhibitors," Bioorg Med Chem Let 16(15):3975-3980, 2006.

Widder et al., ed., Methods in Enzymology (Academic Press, New York) vol. 112, pp. 309-396, 1985.

PCT/US07/66894 Search Report dated Feb. 15, 2008.

STN Abstract of WO 2004083167, Accession # 2004;799553.

PCT/US07/66467 Search Report dated Sep. 29, 2008.

* cited by examiner

N-ARYL-N'ALKYL SULFAMIDES AS MEK INHIBITORS

CROSS-REFERENCE TO RELATED APPLICATIONS

This application claims the benefit of U.S. Provisional Application No. 60/791,290, filed Apr. 11, 2006, which application is incorporated herein by reference.

FIELD OF THE INVENTION

This invention concerns N-(ortho phenylaminoaryl), N'-alkyl sulfamides which are inhibitors of MEK and are useful in the treatment of cancer and other hyperproliferative diseases.

BACKGROUND OF THE INVENTION

Oncogenes—genes that contribute to the production of cancers—are generally mutated forms of certain normal cellular genes ("proto-oncogenes"). Oncogenes often encode abnormal versions of signal pathway components, such as receptor tyrosine kinases, serine-threonine kinases, or downstream signaling molecules. The central downstream signaling molecules are the Ras proteins, which are anchored on the inner surfaces of cytoplasmic membranes, and which hydrolyze bound guanosine triphosphate (GTP) to guanosine diphosphate (GDP). When activated by a growth factor, growth factor receptors initiate a chain of reactions that leads to the activation of guanine nucleotide exchange activity on Ras. Ras alternates between an active "on" state with a bound GTP (hereafter "Ras.GTP") and an inactive "off" state with a bound GDP. The active "on" state, Ras.GTP, binds to and activates proteins that control the growth and differentiation of cells.

For example, in the "mitogen-activated protein kinase (MAP kinase) cascade," Ras.GTP leads to the activation of a cascade of serine/threonine kinases. One of several groups of kinases known to require a Ras.GTP for their own activation is the Raf family. The Raf proteins activate "MEK1" and "MEK2," abbreviations for mitogen-activated ERK-activating kinases (where ERK is extracellular signal-regulated protein kinase, another designation for MAPK). MEK1 and MEK2 are dual-function serine/threonine and tyrosine protein kinases and are also known as MAP kinase kinases. Thus, Ras.GTP activates Raf, which activates MEK1 and MEK2, which activate MAP kinase (MAPK). Activation of MAP kinase by mnitogens appears to be essential for proliferation, and constitutive activation of this kinase is sufficient to induce cellular transformation. Blockade of downstream Ras signaling, as by use of a dominant negative Raf-1 protein, can completely inhibit mitogenesis, whether induced from cell surface receptors or from oncogenic Ras mutants.

The interaction of Raf and Ras is a key regulatory step in the control of cell proliferation. To date, no substrates of MEK other than MAPK have been identified; however, recent reports indicate that MEK may also be activated by other upstream signal proteins such as MEK kinase or MEKK1 and PKC. Activated MAPK translocates and accumulates in the nucleus, where it can phosphorylate and activate transcription factors such as Elk-1 and Sap la, leading to the enhanced expression of genes such as that for c-fos.

Once activated, Raf and other kinases phosphorylate MEK on two neighboring serine residues, $S^{218}$ and $S^{222}$ in the case of MEK-1. These phosphorylations are required for activation of MEK as a kinase. In turn, MEK phosphorylates MAP kinase on two residues separated by a single amino acid: a tyrosine, $Y^{85}$, and a threonine, $T^{183}$. MEK appears to associate strongly with MAP kinase prior to phosphorylating it, suggesting that phosphorylation of MAP kinase by MEK may require a prior strong interaction between the two proteins. Two factors—MEK's unusual specificity and its requirement for a strong interaction with MAP kinase prior to phosphorylation—suggest that MEK's mechanism of action may differ sufficiently from the mechanisms of other protein kinases as to allow for selective inhibitors of MEK. Possibly, such inhibitors would operate through allosteric mechanisms rather than through the more usual mechanism involving blockage of an ATP binding site.

Thus, MEK1 and MEK2 are validated and accepted targets for anti-proliferative therapies, even when the oncogenic mutation does not affect MEK structure or expression. See, for example, U.S. Patent Publications 2003/0149015 by Barrett et al. and 2004/0029898 by Boyle et al.

SUMMARY OF THE INVENTION

This invention provides for compounds of formula I, pharmaceutically acceptable salts, solvates, polymorphs, esters, tautomers or prodrugs thereof,

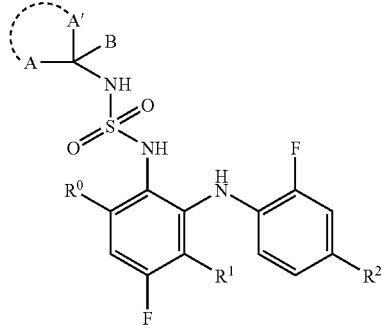

formula I wherein

B is H, $C_1$-$C_4$ alkyl, or $C_2$-$C_6$ alkenyl;
  wherein said $C_1$-$C_4$ alkyl is optionally substituted with one or two hydroxy groups;
A and A' are each independently H, $C_1$-$C_4$ alkyl, or $C_2$-$C_6$ alkenyl;
  wherein said $C_1$-$C_4$ alkyl is optionally substituted with one or two hydroxy groups; or
A and A' together with the carbon atom to which they are attached, form a cyclopropyl, cyclobutyl, or cyclopentyl group, optionally substituted with methyl, hydroxy, or halogen;
$R^1$ is H or F;
$R^2$ is Br or I;
$R^0$ is H, halogen, hydroxy, azido, cyano, cyanomethyl or nitro; or
$R^0$ is $C_1$-$C_6$ alkyl, $C_3$-$C_6$ cycloalkyl, $C_2$-$C_6$ alkenyl, or $C_2$-$C_6$ alkynyl;
  wherein each alkyl, cycloalkyl, alkenyl, or alkynyl group is optionally substituted with 1-3 substituents selected independently from halogen, hydroxy, azido, cyano, cyanomethyl, nitro, phenyl, difluoromethyl, trifluoromethyl, $C_1$-$C_4$ alkoxy and difluoromethoxy; or $R^0$ is phenyl, optionally substituted with halogen, hydroxy, azido, cyano, cyanomethyl, nitro, phenyl, difluoromethyl, trifluoromethyl, methoxy, $C_1$-$C_4$ alkyl, or $C_1$-$C_4$ alkoxy; or $R^0$ is $OR^3$, $O—C(=O)R^4$, $C(=O)OR^5$, $—O—C(O)—NR^6R^7$, $NR^6R^7$, $—NR^8C(=O)NR^9R^{10}$, $—SR^{11}$, $NHC(=O)R^{12}$, $C(=O)NR^9R^{10}$, $NHSO_2R^{13}$, or $SO_2NR^{14}R^{15}$; wherein $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently H, $C_1$-$C_4$ alkyl or phenyl;
  wherein each $C_1$-$C_4$ alkyl or phenyl group is optionally substituted with halogen, hydroxy, azido, cyano, cyanomethyl, nitro, phenyl, difluoromethyl, trifluoromethyl, methoxy, or $C_1$-$C_4$ alkoxy; or $R^0$ is a 5 or 6-atom heterocyclic group, which group may be saturated, unsaturated, or aromatic, containing 1-5 heteroatoms selected independently from O, N, and S, which heterocyclic group is optionally substituted with halogen, hydroxy, azido, cyano, cyanomethyl, nitro, phenyl, difluoromethyl, trifluoromethyl, $C_1$-$C_4$ alkyl, $C_1$-$C_4$ alkoxy or difluoromethoxy; or $R^0$ is a 5- to 10-atom monocyclic or bicyclic heterocyclic group, which group may be saturated, unsaturated, or aromatic, containing 1-5 heteroatoms selected independently from O, N, and S, which heterocyclic group is optionally substituted with halogen, hydroxy, azido, cyano, cyanomethyl, nitro, phenyl, difluoromethyl, trifluoromethyl, $C_1$-$C_4$ alkyl, $C_1$-$C_4$ alkoxy or difluoromethoxy.

In a preferred embodiment, the invention provides for compounds of formula I and their pharmaceutically acceptable salts.

In further or additional embodiments, the invention provides for compounds of formula I and their pharmaceutically acceptable solvates.

In further or additional embodiments, the invention provides for compounds of formula I and their pharmaceutically acceptable polymorphs.

In further or additional embodiments, the invention provides for compounds of formula I and their pharmaceutically acceptable esters.

In further or additional embodiments, the invention provides for compounds of formula I and their pharmaceutically acceptable tautomers.

In further or additional embodiments, the invention provides for compounds of formula I and their pharmaceutically acceptable prodrugs.

In one subgeneric embodiment, the invention provides a compound of formula I, where $R^0$ is $C_1$-$C_6$ alkyl, $C_3$-$C_6$ cycloalkyl, $C_2$-$C_6$ alkenyl, $C_2$-$C_6$ alkynyl, $C_1$-$C_4$ alkoxy, or $NR_6R_7$, where A, A', B, $R_1$, $R_2$, $R_6$, and $R_7$ are defined as for formula I.

In another subgeneric embodiment, the invention provides a compound of formula I, where $R^0$ is $—SR_{11}$, $NHC(=O)R_{12}$, $NHSO_2R_{13}$ and $SO_2NR_{14}R_{15}$, and where A, A', B, $R_1$, $R_2$, and $R_{11}$-$R_{15}$ are defined as for formula I.

In another subgeneric embodiment, this invention provides a compound of formula I, where $R^0$ is $OR_3$, $O—C(=O)R_4$, $C(=O)OR_5$, $—O—C(O)—NR_6R_7$, $—NR_8C(=O)NR_9R_{10}$, and where A, A', B, $R_1$-$R_2$ are defined as for formula I.

In another embodiment, this invention provides a compound of formula I, where $R^0$ is nitro, cyano, cyanomethyl, $—O—C(O)—NR_6R_7$, $NR_6R_7$, $—NR_8C(=O)NR_9R_{10}$, $—SR_1$, $NHC(=O)R_{12}$, $C(=O)NR_9R_{11}$, $NHSO_2R_{13}$, or $SO_2NR_{14}R_{15}$, and where A, A', B, $R_1R_2$, and $R_6$-$R_{15}$ are defined as for formula I.

In another embodiment, this invention provides a compound of formula I where $R^0$ is a 5- to 10-atom monocyclic or bicyclic heterocyclic group, as provided above.

In another subgeneric embodiment, this invention provides a compound of formula I, where $R^0$ is isothiazolyl, isoxazolyl, isoxazolinyl, isoxazolidinyl, oxazolyl, oxazolinyl, oxazolidinyl, thiazolyl, triazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, piperidinyl, pyrimidyl, morpholyl, or tetrahydrofuryl, where A, A', B, and $R_1$-$R_{10}$ are defined as for formula I.

In another subgeneric embodiment, this invention provides a compound of formula I, where $R^0$ is isothiazolyl, isoxazolyl, oxazolyl, thiazolyl, triazolyl, thienyl, furyl, pyrrolyl, or imidazolyl, where A, A', B, and $R_1$-$R_{10}$ are defined as for formula I.

In another subgeneric embodiment, this invention provides a compound of formula I, where $R^0$ is phenyl, o-tolyl, m-tolyl, p-tolyl, o-anisyl, m-anisyl, p-anisyl, or benzyl, where A, A', B, and $R_1$-$R_{10}$ are defined as for formula I.

In another subgeneric embodiment, this invention provides a compound of formula I, where $R^0$ is $CH_3C\equiv C—$, $PhC\equiv C—$, or $Ph$-$CH=CH—$, where A, A', B, and $R_1$-$R_{10}$ are defined as for formula I.

In a subgeneric embodiment, the invention provides a compound of formula I, where $R^0$ is $C_1$-$C_4$ alkyl, $C_2$-$C_5$ alkenyl, $C_3$-$C_6$ cycloalkyl, $C_1$-$C_4$ alkoxy, or $NR_6R_7$, where A, A', B, $R_1$, and $R_2$ are defined as for formula I, and where $R^0$ and $R_7$ are H or $C_1$-$C_4$ alkyl, where all alkyl and alkenyl groups are optionally substituted with 1-3 substituents selected from halogen, hydroxy, and cyano.

In a more specific subgeneric embodiment, this invention provides a compound of formula I, where $R^0$ is isothiazolyl, isoxazolyl, oxazolyl, thiazolyl, triazolyl, thienyl, furyl, pyrrolyl, or imidazolyl, $R_1$ is F, and $R_2$ is I.

In a more specific subgeneric embodiment, this invention provides a compound of formula I, where $R^0$ is phenyl, o-tolyl, m-tolyl, p-tolyl, o-anisyl, m-anisyl, p-anisyl, or benzyl, $R_1$ is F, and $R_2$ is I.

In a more specific subgeneric embodiment, this invention provides a compound of formula I, where $R^0$ is $CH_3C\equiv C—$, $PhC\equiv C—$, or $Ph$-$CH=CH—$, $R_1$ is F, and $R_2$ is I.

In a more specific subgeneric embodiment, the invention provides a compound of formula I, where $R^0$ is $C_1$-$C_4$ alkyl, $C_2$-$C_5$ alkenyl, $C_3$-$C_6$ cycloalkyl, $C_1$-$C_4$ alkoxy, or $NR_6R_7$, $R_1$ is F, and $R_2$ is I, where A, A' and B are defined as for formula I, and where $R_6$ and $R_7$ are H or $C_1$-$C_4$ alkyl, where all alkyl and alkenyl groups are optionally substituted with 1-3 substituents selected from halogen, hydroxy, and cyano.

In a more specific subgeneric embodiment, the invention provides a compound of formula I, where $R^0$ is $C_1$-$C_4$ alkyl or $C_1$-$C_4$ alkoxy, optionally substituted with halogen or cyano, $R_1$ is F, and $R_2$ is I, where A, A' and B are defined as for formula I.

In a subgeneric embodiment, the invention provides a compound of formula I, where $R^0$ is methyl, ethyl, isopropyl, trifluoromethyl, cyanomethyl, sec-butyl, iso-butyl, tert-butyl, acetyl, acetamido, methylcarbamoyl, methoxy, methylamino, or dimethylamino, where all alkyl groups are optionally substituted with 1-3 halogen atoms; where A, A', and B are defined as above for formula I; where $R_1$ is F; and where $R_2$ is I.

In a subgeneric embodiment, the invention provides a compound of formula I, where $R^0$ is methyl, ethyl, isopropyl, trifluoromethyl, cyanomethyl, sec-butyl, iso-butyl, tert-butyl, acetyl, acetamido, methylcarbamoyl, methoxy, methylamino, or dimethylamino, where all alkyl groups are optionally substituted with 1-3 halogen atoms; where A and A' are both H or together A and A1 are $—CH_2—CH_2—$; where B is H, $CH_3$, $CH_2CH_2OH$, $CH_2CH(OH)CH_2OH$, $CH_2—CH=CH_2$, $(CH_2)_2CH(OH)CH_2OH$, or $—CH_2—CH_2—CH=CH_2$; where $R_1$ is F; and where $R_2$ is I.

In another subgeneric embodiment, the invention provides a compound of formula I, where $R^0$ is methyl, ethyl, isopropyl, trifluoromethyl, cyanomethyl, sec-butyl, iso-butyl, tert-butyl, acetyl, acetamido, methylcarbamoyl, methoxy, methylamino, or dimethylamino, where all alkyl groups are optionally substituted with 1-3 halogen atoms; where A and A' are both H or together A and A' are —CH$_2$—CH$_2$—CH$_2$— —CH$_2$—CH$_2$—, —CH$_2$—CH(CH$_3$)— or —CH$_2$—CHCl—; where B is H, CH$_3$, CH$_2$CH$_2$OH, CH$_2$CH(OH)CH$_2$OH, (CH$_2$)$_2$CH(OH)CH$_2$OH, CH$_2$—CH=CH$_2$ or —CH$_2$—CH$_2$—CH=CH$_2$; where $R_1$ is F; and where $R_2$ is Br.

In another embodiment, this invention provides a compound of formula I, where $R^0$ is isothiazolyl, isoxazolyl, oxazolyl, thiazolyl, triazolyl, thienyl, furyl, pyrrolyl, or imidazolyl; where A, A' are both H or together are —CH$_2$—CH$_2$—CH$_2$—, —CH$_2$—CH$_2$— —CH$_2$—CH(CH$_3$)—, or —CH$_2$—CHCl—; B is H, CH$_3$, CH$_2$CH$_2$OH, CH$_2$CH(OH)CH$_2$OH, (CH$_2$)$_2$CH(OH)CH$_2$OH, CH$_2$—CH=CH$_2$ or —CH$_2$—CH$_2$—CH=CH$_2$; $R_1$ is F and $R_2$ is I. In some embodiments, $R_1$ is a 5 or 6-atom heterocyclic group, which group may be saturated, unsaturated, or aromatic, containing 1-5 heteroatoms selected independently from O, N, and S, which heterocyclic group is optionally substituted with $C_1$-$C_4$ alkyl, halogen, hydroxy, or $C_1$-$C_4$ alkoxy.

In further or additional embodiments $R^0$ is isothiazolyl, isoxazolyl, isoxazolinyl, isoxazolidinyl, oxazolyl, oxazolinyl, oxazolidinyl, thiazolyl, triazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, piperidinyl, pyrimidyl, morpholyl, or tetrahydrofuryl, optionally substituted with $C_1$-$C_4$ alkyl, halogen, hydroxy, or $C_1$-$C_4$ alkoxy.

In further or additional embodiments $R^0$ is $C_1$-$C_6$ alkyl, $C_3$-$C_6$ cycloalkyl, $C_2$-$C_6$ alkenyl or $C_2$-$C_6$ alkynyl, wherein each alkyl, cycloalkyl, alkenyl, or alkynyl group is optionally substituted with 1-3 substituents selected independently from halogen, hydroxy, azido, cyano, cyanomethyl, nitro, phenyl, difluoromethyl, trifluoromethyl, $C_1$-$C_4$ alkoxy and difluoromethoxy; or $R^0$ is $OR^3$ or $NR_6R_7$; $R^3$ is $C_1$-$C_4$ alkyl; and $R^6$ and $R^7$ are each independently H, $C_1$-$C_4$ alkyl or phenyl, wherein each $C_1$-$C_4$ alkyl or phenyl group is optionally substituted with halogen, methyl, trifluoromethyl, hydroxy, or alkoxy.

In further or additional embodiments B is —H, —CH$_3$, —CH$_2$CH$_2$OH, —CH$_2$CH(OH)CH$_2$OH, —(CH$_2$)$_2$CH(OH)CH$_2$OH, —CH$_2$—CH=CH$_2$ or —CH$_2$—CH$_2$CH=CH$_2$; and A and A' are both H; or A and A' together with the carbon atom to which they are attached are

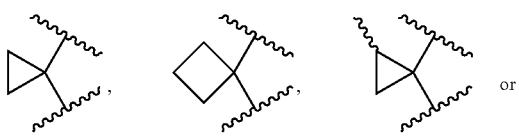

or

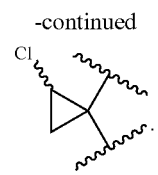

-continued

In further or additional embodiments $R^0$ is a 5 or 6-atom heterocyclic group, which group may be saturated, unsaturated, or aromatic, containing 1-5 heteroatoms selected independently from O, N, and S, which heterocyclic group is optionally substituted with $C_1$-$C_4$ alkyl, halogen, hydroxy, or $C_1$-$C_4$ alkoxy; B is —H, —CH$_3$, —CH$_2$CH$_2$OH, —CH$_2$CH(OH)CH$_2$OH, —(CH$_2$)$_2$CH(OH)CH$_2$OH, —CH$_2$—CH=CH$_2$ or —CH$_2$—CH$_2$CH=CH$_2$; and A and A' are both H; or A and A' together with the carbon atom to which they are attached are

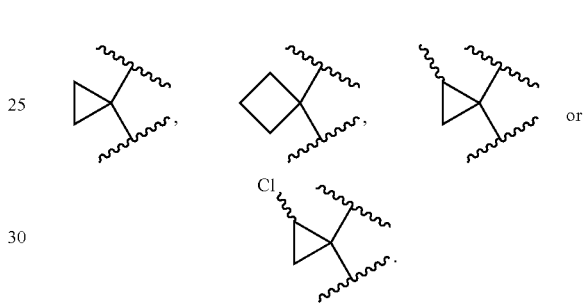

In further or additional embodiments $R^0$ is isothiazolyl, isoxazolyl, isoxazolinyl, isoxazolidinyl, oxazolyl, oxazolinyl, oxazolidinyl, thiazolyl, triazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, piperidinyl, pyrimidyl, morpholyl, or tetrahydrofuryl, optionally substituted with $C_1$-$C_4$ alkyl, halogen, hydroxy, or $C_1$-$C_4$ alkoxy; B is —H, —CH$_3$, —CH$_2$CH$_2$OH, —CH$_2$CH(OH)CH$_2$OH, —(CH$_2$)$_2$CH(OH)CH$_2$OH, —CH$_2$—CH=CH$_2$ or —CH$_2$—CH$_2$CH=CH$_2$; and A and A' are both H; or A and A' together with the carbon atom to which they are attached are

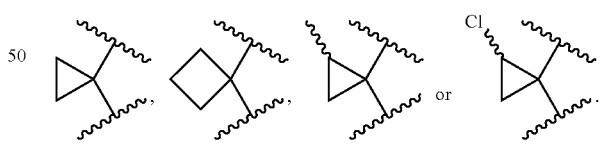

In further or additional embodiments, the compound of formula I is selected from those given in the list below:

| CPD # | —C(A)A'— | —B | $R^0$ | $R^1$ | $R^2$ |
|---|---|---|---|---|---|
| 1 | —CH$_2$— | —H | OCH$_3$ | F | I |
| 2 | —CH$_2$— | —H | NHCH$_3$ | F | I |
| 3 | —CH$_2$— | —H | CH$_2$CH$_3$ | F | I |
| 4 | —CH$_2$— | —H | CH$_2$CH=CH$_2$ | F | I |
| 5 | —CH$_2$— | —H | CN | F | I |

-continued

| CPD # | —C(A)A'— | —B | R⁰ | R¹ | R² |
|---|---|---|---|---|---|
| 6 | —CH₂— | —H | CF₃ | F | I |
| 7 | —CH₂— | —H | Cl | F | I |
| 8 | —CH₂— | —H | C₆H₅ | F | I |
| 9 | —CH₂— | —CH₂CH(OH)CH₂OH | OCH₃ | F | I |
| 10 | —CH₂— | —CH₂CH(OH)CH₂OH | NHCH₃ | F | I |
| 11 | —CH₂— | —CH₂CH(OH)CH₂OH | CH₂CH₃ | F | I |
| 12 | cyclopropyl | —CH₂—CH₂—CH=CH₂ | OCH₃ | F | I |
| 13 | cyclopropyl | —CH₂—CH₂—CH=CH₂ | NHCH₃ | F | I |
| 14 | cyclopropyl | —CH₂—CH₂—CH=CH₂ | CH₂CH₃ | F | I |
| 15 | cyclopropyl | —CH₃ | H | F | I |
| 16 | cyclopropyl | —CH₂CH₂OH | H | F | I |
| 17 | cyclopropyl | —(CH2)₂CH(OH)CH₂OH | H | F | I |
| 18 | CH(CH₃) | —(CH₂)₂CH(OH)CH₂OH | H | F | I |
| 19 | cyclopropyl | —CH₃ | OCH₃ | F | I |
| 20 | cyclopropyl | —CH₂CH₂OH | OCH₃ | F | I |
| 21 | cyclopropyl | —(CH₂)₂CH(OH)CH₂OH | OCH₃ | F | I |

-continued
| CPD # | —C(A)A'— | —B | R⁰ | R¹ | R² |
|---|---|---|---|---|---|
| 22 | 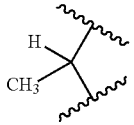 | —(CH$_2$)$_2$CH(OH)CH$_2$OH | OCH$_3$ | F | I |
| 23 | 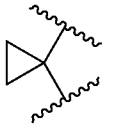 | —CH$_3$ | CF$_3$ | F | I |
| 24 | 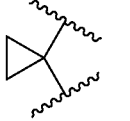 | —CH$_2$CH$_2$OH | CF$_3$ | F | I |
| 25 | 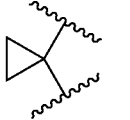 | —(CH$_2$)$_2$CH(OH)CH$_2$OH | OCH$_3$ | F | I |
| 26 | 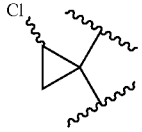 | —CH$_2$CH(OH)CH$_2$OH | OCH$_3$ | F | I |
| 27 | 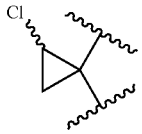 | —H | OCH$_3$ | F | I |
| 28 | 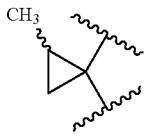 | —H | CH=CH$_2$ | F | I |
| 29 | 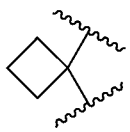 | —CH$_2$CH(OH)CH$_2$OH | OCH$_3$ | F | I |
| 30 | 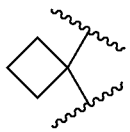 | —CH$_2$CH(OH)CH$_2$OH | NHCH$_3$ | F | I |
| 31 | 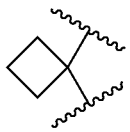 | —CH$_2$CH(OH)CH$_2$OH | CH$_2$CH$_3$ | F | I |
| 32 | 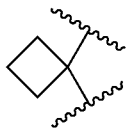 | —CH$_2$CH(OH)CH$_2$OH | CH$_2$CH=CH$_2$ | F | I |

-continued

| CPD # | —C(A)A'— | —B | R⁰ | R¹ | R² |
|---|---|---|---|---|---|
| 33 | 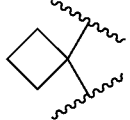 | —CH₂CH(OH)CH₂OH | N(CH₃)₂ | F | I |
| 34 | 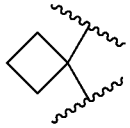 | —CH₂—CH₂—CH=CH₂ | OCH₃ | F | I |
| 35 | 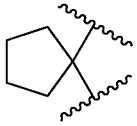 | —CH₂—CH₂—CH=CH₂ | NHCH₃ | F | I |
| 36 | 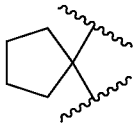 | —CH₂—CH₂—CH=CH₂ | CH₂CH₃ | F | I |
| 37 | 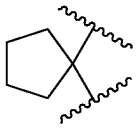 | —CH₃ | CH=CH₂ | F | I |
| 38 | 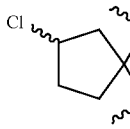 | —CH₂CH₂OH | OCH₃ | F | I |
| 39 | 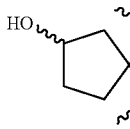 | —(CH₂)₂CH(OH)CH₂OH | NHCH₃ | F | I |
| 40 | 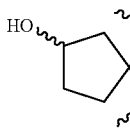 | —CH₃ | OCH₃ | F | I |
| 41 | —CH₂— | —H | OCH₃ | H | I |
| 42 | —CH₂— | —H | NHCH₃ | H | I |
| 43 | —CH₂— | —H | CH₂CH₃ | H | I |
| 44 | —CH₂— | —H | CH₂CH=CH₂ | H | I |
| 45 | —CH₂— | —H | CN | H | Br |
| 46 | —CH₂— | —H | CF₃ | H | Br |
| 47 | —CH₂— | —H | Cl | H | Br |
| 48 | —CH₂— | —H | C₆H₅ | H | Br |
| 49 | —CH₂— | —CH₂CH(OH)CH₂OH | OCH₃ | H | Br |
| 50 | —CH₂— | —CH₂CH(OH)CH₂OH | NHCH₃ | H | Br |
| 51 | —CH₂— | —CH₂CH(OH)CH₂OH | CH₂CH₃ | H | Br |
| 52 | 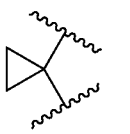 | —CH₂—CH₂—CH=CH₂ | OCH₃ | H | I |

-continued

| CPD # | —C(A)A'— | —B | R⁰ | R¹ | R² |
|---|---|---|---|---|---|
| 53 | cyclopropyl | —CH₂—CH₂—CH=CH₂ | NHCH₃ | H | I |
| 54 | cyclopropyl | —CH₂—CH₂—CH=CH₂ | CH₂CH₃ | H | I |
| 55 | cyclopropyl | —CH₃ | 4-imidazolyl | H | I |
| 56 | cyclopropyl | —CH₂CH₂OH | 4-thiazolyl | H | I |
| 57 | cyclopropyl | —(CH₂)₂CH(OH)CH₂OH | 2-oxazolyl | H | I |
| 58 | CH(CH₃) | —(CH₂)₂CH(OH)CH₂OH | 2-furanyl | H | I |
| 59 | cyclopropyl | —CH₃ | OCH₃ | H | Br |
| 60 | cyclopropyl | —CH₂CH₂OH | OCH₃ | H | Br |
| 61 | cyclopropyl | —(CH₂)₂CH(OH)CH₂OH | OCH₃ | H | Br |
| 62 | CH(CH₃) | —(CH₂)₂CH(OH)CH₂OH | OCH₃ | H | Br |
| 63 | —CH₂— | —H | 4-imidazolyl | F | I |
| 64 | —CH₂— | —CH₃ | 4-thiazolyl | F | I |
| 65 | —CH₂— | —CH₂CH₂OH | 2-oxazolyl | F | I |
| 66 | —CH₂— | —(CH₂)₂CH(OH)CH₂OH | 2-furanyl | F | I |
| 67 | —CH₂— | —H | 1,2,3-triazolyl-4-yl | F | I |
| 68 | —CH₂— | —H | 2-thienyl | F | I |
| 69 | —CH₂— | —H | 3-isothiazolyl | F | I |

-continued

| CPD # | —C(A)A'— | —B | R⁰ | R¹ | R² |
|---|---|---|---|---|---|
| 70 | —CH₂— | —H | 4-isothiazolyl | F | I |
| 71 | —CH₂— | —H | 3-isoxazolyl | F | I |
| 72 | 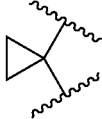 | —CH₃ | 4-imidazolyl | H | Br |
| 73 | 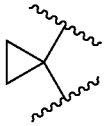 | —CH₂CH₂OH | 4-thiazolyl | H | Br |
| 74 | 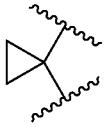 | —(CH₂)₂CH(OH)CH₂OH | 2-oxazolyl | H | Br |
| 75 | 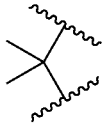 | —(CH₂)₂CH(OH)CH₂OH | 2-furanyl | H | Br |
| 76 | 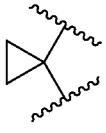 | —CH₃ | 1,2,3-triazolyl-4-yl | H | Br |
| 77 | 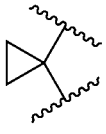 | —CH₂CH₂OH | 4-imidazolyl | H | Br |
| 78 | —CH₂— | —(CH₂)₂CH(OH)CH₂OH | 3-isothiazolyl | F | Br |
| 79 | —CH₂— | —H | 4-isothiazolyl | F | Br |
| 80 | —CH₂— | —H | 3-isoxazolyl | F | Br |
| 81 | 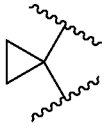 | —CH₃ | 4-imidazolyl | F | Br |
| 82 | 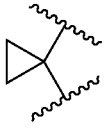 | —CH₂CH₂OH | 4-thiazolyl | F | Br |
| 83 | 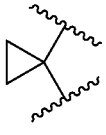 | —(CH₂)₂CH(OH)CH₂OH | 2-oxazolyl | F | Br |

This invention is also directed to pharmaceutical compositions comprising effective amounts of a compound of formula I or a pharmaceutically acceptable salt, solvate, polymorph, ester, tautomer or prodrug thereof. In some embodiments, the pharmaceutical compositions further comprise a pharmaceutically acceptable carrier. Such compositions may contain adjuvants, excipients, preservatives, agents for delaying absorption, fillers, binders, adsorbents, buffers, disintegrating agents, solubilizing agents, other carriers, and other inert ingredients. Methods of formulation of such compositions are well-known in the art.

The invention is also directed to a method of treating a hyperproliferative disorder in a mammal, including a human, comprising administering to said mammal a therapeutically effective amount of the compound of formula I or a pharmaceutically acceptable salt, solvate, polymorph, ester, tautomer or prodrug thereof.

This invention is also directed to a method of treating an inflammatory disease, condition, or disorder in a mammal, including a human, comprising administering to said mammal a therapeutically effective amount of the compound of formula I, or a pharmaceutically acceptable salt, ester, prodrug, solvate, hydrate or derivative thereof.

The invention is also directed to a method of treating a disorder or condition which is modulated by the MEK cascade in a mammal, including a human, comprising administering to said mammal an amount of the compound of formula I, or a pharmaceutically acceptable salt, ester, prodrug, solvate, hydrate or derivative thereof, effective to modulate said cascade. The appropriate dosage for a particular patient can be determined, according to known methods, by those skilled in the art.

In other aspects, the present invention is directed to a pharmaceutical composition comprising a compound of formula I or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.002 to about 6 g/day. In further or additional embodiments the amount of compound of formula I is about 0.005 to about 5 g/day. In further or additional embodiments the amount of compound of formula I is about 0.01 to about 5 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the pharmaceutical composition is for administration to a mammal. In further or additional embodiments, the mammal is human. In further or additional embodiments, the pharmaceutical composition further comprises a pharmaceutical carrier, excipient and/or adjuvant. In further or additional embodiments, the pharmaceutical composition further comprises at least one therapeutic agent In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is taxol, bortezomib or both. In further or additional embodiments, the pharmaceutical composition is administered in combination with an additional therapy. In further or additional embodiments, the additional therapy is radiation therapy, chemotherapy or a combination of both. In further or additional embodiments, the pharmaceutical composition comprises a pharmaceutically acceptable salt of a compound of formula I.

In other aspects, the present invention is directed to a method for inhibiting a MEK enzyme. In some embodiments, the method comprises contacting said MEK enzyme with an amount of a composition comprising a compound of formula I or a pharmaceutically acceptable salt, solvate, polymorph, ester, tautomer or prodrug thereof, sufficient to inhibit said enzyme, wherein said enzyme is inhibited. In further or additional embodiments the enzyme is at least about 1% inhibited. In further or additional embodiments the enzyme is at least about 2% inhibited. In further or additional embodiments the enzyme is at least about 3% inhibited. In further or additional embodiments the enzyme is at least about 4% inhibited. In further or additional embodiments the enzyme is at least about 5% inhibited. In further or additional embodiments the enzyme is at least about 10% inhibited. In further or additional embodiments the enzyme is at least about 20% inhibited. In further or additional embodiments the enzyme is at least about 25% inhibited. In further or additional embodiments the enzyme is at least about 30% inhibited. In further or additional embodiments the enzyme is at least about 40% inhibited. In further or additional embodiments the enzyme is at least about 50% inhibited. In further or additional embodiments the enzyme is at least about 60% inhibited. In further or additional embodiments the enzyme is at least about 70% inhibited. In further or additional embodiments the enzyme is at least about 75% inhibited. In further or additional embodiments the enzyme is at least about 80% inhibited. In further or additional embodiments the enzyme is at least about 90% inhibited. In further or additional embodiments the enzyme is essentially completely inhibited. In further or additional embodiments the MEK enzyme is MEK kinase. In further or additional embodiments the MEK enzyme is MEK1. In further or additional embodiments the MEK enzyme is MEK2. In further or additional embodiments the contacting occurs within a cell. In further or additional embodiments the cell is a mammalian cell. In further or additional embodiments the mammalian cell is a human cell. In further or additional embodiments, the MEK enzyme is inhibited with a composition comprising a pharmaceutically acceptable salt of a compound of formula I.

In some aspects, the present invention is directed to a method of treating a disease in an individual suffering from said disease comprising administering to said individual an effective amount of a composition comprising a compound of formula I or a pharmaceutically acceptable salt, solvate, polymorph, ester, tautomer or prodrug thereof.

In other aspects, the present invention is directed to a method of treatment of a MEK mediated disorder in an individual suffering from said disorder comprising administering to said individual an effective amount of a composition comprising a compound of formula I or a pharmaceutically acceptable salt, solvate, polymorph, ester, tautomer or prodrug thereof. In some embodiments, the composition comprising a compound of formula I is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release formulations, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the MEK mediated disorder is a mammal. In further or additional embodiments, the individual is a human. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the MEK mediated disorder is selected from the group consisting of inflammatory diseases, infections, autoimmune disorders, stroke, ischemia, cardiac disorder, neurological disorders, fibrogenetic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma and wide angle glaucoma. In further or additional embodiments, the MEK mediated disorder is an inflammatory disease. In further or additional embodiments, the MEK mediated disorder is a hyperproliferative disease. In further or additional embodiments, the MEK mediated disorder is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, an effective amount of a composition comprising a pharmaceutically acceptable salt of a compound of formula I is administered.

In other aspects, the present invention is directed to a method for degrading, inhibiting the growth of or killing a cancer cell comprising contacting said cell with an amount of a composition effective to degrade, inhibit the growth of or to kill said cell, the composition comprising a compound of formula I or a pharmaceutically acceptable salt, solvate, polymorph, ester, tautomer or prodrug thereof. In some embodiments, the cancer cells comprise brain, breast, lung, ovarian, pancreatic, prostate, renal, or colorectal cancer cells. In further or additional embodiments, the composition is administered with at least one therapeutic agent. In further or additional embodiments, the therapeutic agent is taxol, bortezomib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/ anti-hormonal therapeutic agents, and haematopoietic growth factors. In some embodiments, the cancer cells are degraded. In further or additional embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded. In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 10% of the cancer cells are killed. In further or additional embodiments, 20% of the cancer cells are killed. In further or additional embodiments, 25% of the cancer cells are killed. In further or additional embodiments, 30% of the cancer cells are killed. In further or additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In further or additional embodiments, essentially all of the cancer cells are killed. In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In further or additional embodiments, the growth of the cancer cells is about 25% inhibited. In further or additional embodiments, the growth of the cancer cells is about 30% inhibited. In further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited. In further or additional embodiments, a composition comprising a pharmaceutically acceptable salt of a compound of formula I is used.

In other aspects, the present invention is directed to a method for the treatment or prophylaxis of a proliferative disease in an individual comprising administering to said individual an effective amount of a composition comprising a compound of formula I or a pharmaceutically acceptable salt, solvate, polymorph, ester, tautomer or prodrug thereof. In some embodiments, the proliferative disease is cancer, psoriasis, restenosis, autoimmune disease, or atherosclerosis. In further or additional embodiments, the proliferative disease is a hyperproliferative disease. In further or additional embodiments, the proliferative disease is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphona. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/ anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the proliferative disease is a mammal. In further or additional embodiments, the individual is a human. In further or additional embodiments, an effective amount of a composition comprising a pharmaceutically acceptable salt of a compound of formula I is administered.

In other aspects, the present invention is directed to a method for the treatment or prophylaxis of an inflammatory disease in an individual comprising administering to said individual an effective amount of a composition comprising a compound of formula I or a pharmaceutically acceptable salt, solvate, polymorph, ester, tautomer or prodrug thereof. In further or additional embodiments, the inflammatory disease is selected from chronic inflammatory diseases, rheumatoid arthritis, rheumatoid arthritis, spondyloarthropathies, gouty arthritis, osteoarthritis, juvenile arthritis, acute rheumatic arthritis, enteropathic arthritis, neuropathic arthritis, psoriatic arthritis, pyogenic arthritis, atherosclerosis, systemic lupus erythematosus, inflammatory bowel disease, irritable bowel syndrome, ulcerative colitis, reflux esophagitis, Crohn's disease, gastritis, asthma, allergies, respiratory distress syndrome, pancreatitis, chronic obstructive pulmonary disease, pulmonary fibrosis, psoriasis, eczema or scleroderma. In some embodiments, the composition comprising a compound of formula I is administered in combination with an additional therapy. In further or additional embodiments, the composition comprising a compound of formula I is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the inflammatory disease is a mammal. In further or additional embodiments, the individual is a human. In further or additional embodiments, an effective amount of a composition comprising a pharmaceutically acceptable salt of a compound of formula I is administered.

In other aspects, the present invention is directed to a method for the treatment or prophylaxis of cancer in an individual comprising administering to said individual an effective amount of a composition comprising a compound of formula I or a pharmaceutically acceptable salt, solvate, polymorph, ester, tautomer or prodrug thereof. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method of reducing the size of a tumor, inhibiting tumor size increase, reducing tumor proliferation or preventing tumor proliferation in an individual, comprising administering to said individual an effective amount of a composition comprising a compound of formula I or a pharmaceutically acceptable salt, solvate, polymorph, ester, tautomer or prodrug thereof. In some embodiments, the size of a tumor is reduced. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase. In some embodiments, tumor proliferation is reduced. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 75%. In some embodiments, tumor proliferation is reduced by at least 80%. In some embodiments, tumor proliferation is reduced by at least 90%. In some embodiments, tumor proliferation is reduced by at least 95%. In some embodiments, tumor proliferation is prevented. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method for achieving an effect in a patient comprising the administration of an effective amount of a composition comprising a compound of formula I or a pharmaceutically acceptable salt, solvate, polymorph, ester, tautomer or prodrug thereof, to a patient, wherein the effect is selected from the group consisting of inhibition of various cancers, immunological diseases, and inflammatory diseases. In some embodiments, the effect is inhibition of various cancers. In further or additional embodiments, the effect is inhibition of immunological diseases. In further or additional embodiments, the effect is inhibition inflammatory diseases. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein such embodiments are provided by way of example only. It should be understood that various alternatives to the embodiments of the invention described herein may be employed in practicing the invention. Those skilled in the art will appreciate that numerous variations, changes, and substitutions are possible without departing from the invention. It is intended that the following claims define the scope of aspects of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, —CH$_2$O— is equivalent to —OCH$_2$—.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Techniques for inverting or leaving unchanged a particular stereocenter, and those for resolving mixtures of stereoisomers are well known in the art and it is well within the ability of one of skill in the art to choose an appropriate method for a particular situation. See, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, Acc. Chem. Res. 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "catalytic group" refers to a chemical functional group that assists catalysis by acting to lower the activation barrier to reaction.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "A and A' together with the carbon atom to which they are attached, form a cyclopropyl, cyclobutyl, or cyclopentyl group", as used herein, refers to the following:

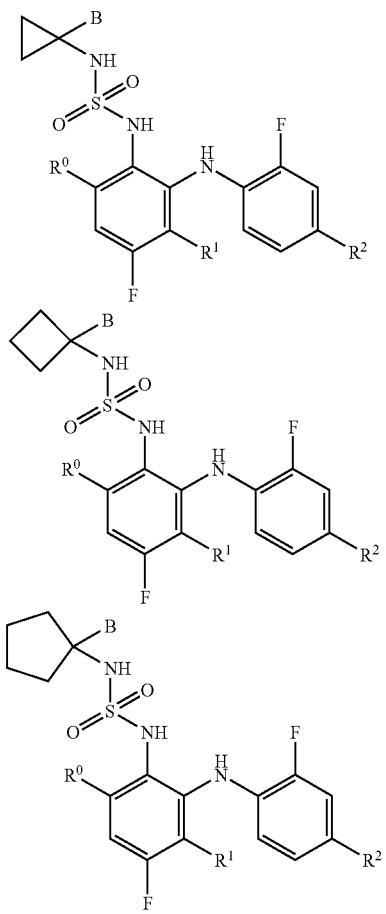

The term "hydrocarbon" as used herein, alone or in combination, refers to a compound or chemical group containing only carbon and hydrogen atoms.

The terms "heteroatom" or "hetero" as used herein, alone or in combination, refer to an atom other than carbon or hydrogen. Heteroatoms are may be independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkylene" as used herein, alone or in combination, refers to a diradical derived from the above-defined monoradical, alkyl. Examples include, but are not limited to methylene (—$CH_2$—), ethylene (—$CH_2CH_2$—), propylene (—$CH_2CH_2CH_2$—), isopropylene (—$CH(CH_3)CH_2$—) and the like.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkenylene" as used herein, alone or in combination, refers to a diradical derived from the above-defined monoradical alkenyl. Examples include, but are not limited to ethenylene (—CH=CH—), the propenylene isomers (e.g., —$CH_2$CH=CH— and —C($CH_3$)=CH—) and the like.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The term "alkynylene" as used herein, alone or in combination, refers to a diradical derived from the above-defined monoradical, alkynyl. Examples include, but are not limited to ethynylene (—C≡C—), propargylene (—$CH_2$—C≡C—) and the like.

The term "aliphatic" as used herein, alone or in combination, refers to an optionally substituted, straight-chain or branched-chain, non-cyclic, saturated, partially unsaturated, or fully unsaturated nonaromatic hydrocarbon. Thus, the term collectively includes alkyl, alkenyl and alkynyl groups.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, =N—N=, —N=N—, —N=N—NH—, —P(O)₂—, —O—P(O)₂—, —P(O)₂—O—, —S(O)—, —S(O)₂—, —SnH₂— and the like.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The term "perhalo" as used herein, alone or in combination, refers to groups in which all of the hydrogen atoms are replaced by fluorines, chlorines, bromines, iodines, or combinations thereof. Thus, as a non-limiting example, the term "perhaloalkyl" refers to an alkyl group, as defined herein, in which all of the H atoms have been replaced by fluorines, chlorines, bromines or iodines, or combinations thereof. A non-limiting example of a perhaloalkyl group is bromo, chloro, fluoromethyl. A non-limiting example of a perhaloalkenyl group is trichloroethenyl. A non-limiting example of a perhaloalkynyl group is tribromopropynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl). Whenever it appears herein, a numerical range such as "C₃-C₆ cycloalkyl" or "C₃₋₆ cycloalkyl", means that the cycloalkyl group may consist of 3 carbon atoms, 4 carbon atoms, 5 carbon atoms or 6 carbon atoms, i.e., is cyclopropyl, cyclobutyl, cyclopentyl or cyclohepty, although the present definition also covers the occurrence of the term "cycloalkyl" where no numerical range is designated. The term includes fused, non-fused, bridged and spiro radicals. A fused cycloalkyl may contain from two to four fused rings where the ring of attachment is a cycloalkyl ring, and the other individual rings may be alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

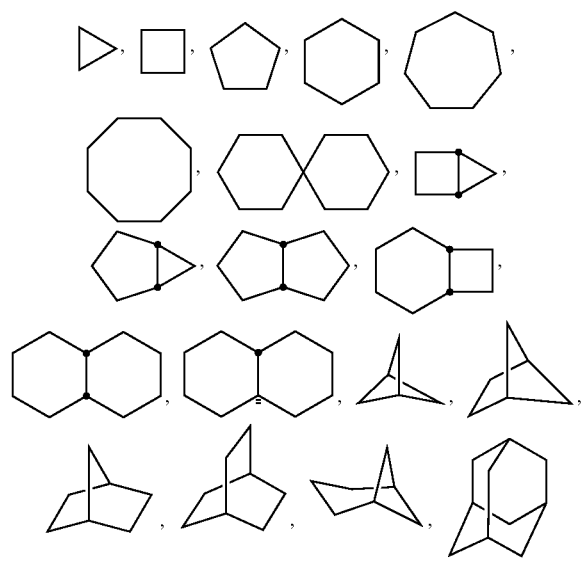

and the like.

The term "cycloalkenyl" as used herein, alone or in combination, refers to an optionally substituted hydrocarbon non-aromatic, monoradical ring, having one or more carbon-carbon double-bonds and from three to about twenty ring carbon atoms, three to about twelve ring carbon atoms, or from three to about ten ring carbon atoms. The term includes fused, non-fused, bridged and Spiro radicals. A fused cycloalkenyl may contain from two to four fused rings where the ring of attachment is a cycloalkenyl ring, and the other individual rings may be alicyclic, heterocyclic, aromatic, heteroaromatic or any combination thereof. Fused ring systems may be fused across a bond that is a carbon-carbon single bond or a carbon-carbon double bond. Examples of cycloalkenyls include, but are not limited to cyclohexenyl, cyclopentadienyl and bicyclo[2.2.1]hept-2-ene ring systems. Illustrative examples include, but are not limited to the following moieties:

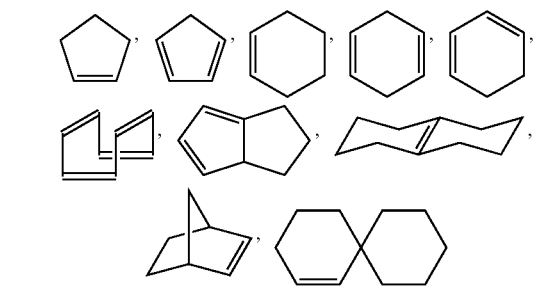

and the like.

The terms "alicyclyl" or "alicyclic" as used herein, alone or in combination, refer to an optionally substituted, saturated, partially unsaturated, or fully unsaturated nonaromatic hydrocarbon ring systems containing from three to about twenty ring carbon atoms, three to about twelve ring carbon atoms, or from three to about ten ring carbon atoms. Thus, the terms collectively include cycloalkyl and cycloalkenyl groups.

The terms "non-aromatic heterocyclyl" and "heteroalicyclyl" as used herein, alone or in combination, refer to optionally substituted, saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. In embodiments in which two or more heteroatoms are present in the ring, the two or more heteroatoms can be the same as each another, or some or all of the two or more heteroatoms can each be different from the others. The terms include fused, non-fused, bridged and Spiro radicals. A fused non-aromatic heterocyclic radical may contain from two to four fused rings where the attaching ring is a non-aromatic heterocycle, and the other individual rings may be alicyclic, heterocyclic, aromatic, heteroaromatic or any combination thereof. Fused ring systems may be fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. Attachment of a non-aromatic heterocyclic subunit to its parent molecule can be via a heteroatom or a carbon atom. Likewise, additional substitution can be via a heteroatom or a carbon atom. As a non-limiting example, an imidazolidine non-aromatic heterocycle may be attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

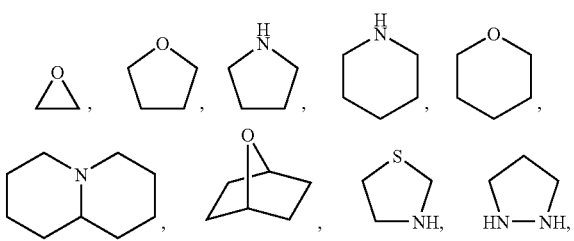

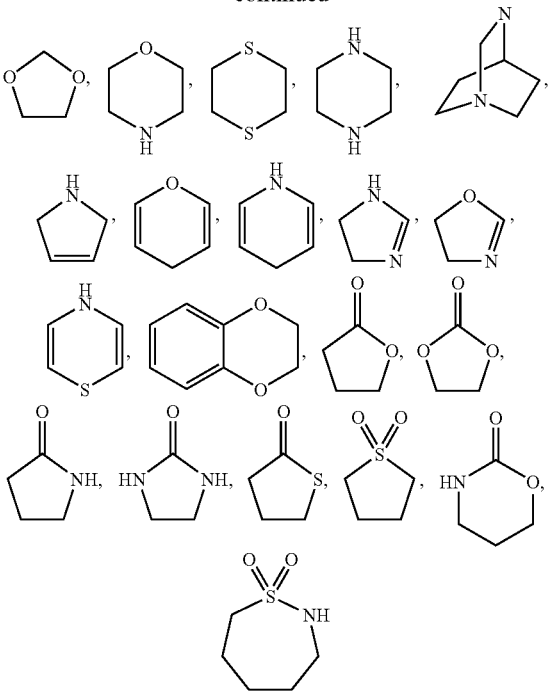

and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized π-electron system containing 4n+2π electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "arylene" as used herein, alone or in combination, refers to a diradical derived from the above-defined monoradical, aryl. Examples include, but are not limited to 1,2-phenylene, 1,3-phenylene, 1,4-phenylene, 1,2-naphthylene and the like.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidiazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

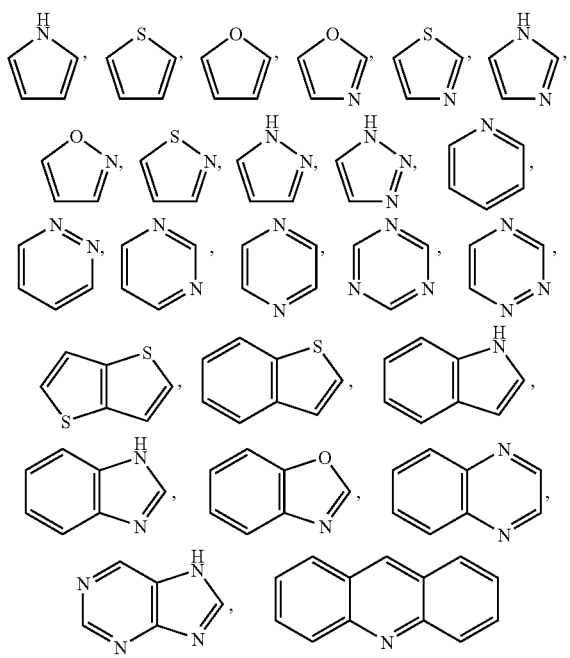

and the like.

The term "heteroarylene" as used herein, alone or in combination, refers to a diradical derived from the above-defined monoradical heteroaryl. Examples include, but are not limited to pyridinyl and pyrimidinyl.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Heterocycles can be optionally substituted. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom.

The term "carbocyclyl" as used herein, alone or in combination, refers collectively to alicyclyl and aryl groups; i.e. all carbon, covalently closed ring structures, which may be saturated, partially unsaturated, fully unsaturated or aromatic. Carbocyclic rings can be formed by three, four, five, six, seven, eight, nine, or more than nine carbon atoms. Carbocycles can be optionally substituted. The term distinguishes carbocyclic from heterocyclic rings in which the ring backbone contains at least one atom which is different from carbon.

The terms "halogen", "halo" or "halide" as used herein, alone or in combination refer to fluoro, chloro, bromo and iodo.

The term "hydroxy" as used herein, alone or in combination, refers to the monoradical —OH.

The term "cyano" as used herein, alone or in combination, refers to the monoradical —CN.

The term "cyanomethyl" as used herein, alone or in combination, refers to the monoradical —CH$_2$CN.

The term "nitro" as used herein, alone or in combination, refers to the monoradical —NO$_2$.

The term "oxy" as used herein, alone or in combination, refers to the diradical —O—.

The term "oxo" as used herein, alone or in combination, refers to the diradical =O.

The term "carbonyl" as used herein, alone or in combination, refers to the diradical —C(=O)—, which may also be written as —C(O)—.

The terms "carboxy" or "carboxyl" as used herein, alone or in combination, refer to the moiety —C(O)OH, which may also be written as —COOH.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups may be optionally substituted, and wherein the terms alkyl, aliphatic and carbocyclyl are as defined herein. Non-limiting examples of alkyloxy radicals include methoxy, ethoxy, n-propoxy, isopropoxy, n-butoxy, iso-butoxy, sec-butoxy, tert-butoxy and the like.

The term "sulfinyl" as used herein, alone or in combination, refers to the diradical —S(=O)—.

The term "sulfonyl" as used herein, alone or in combination, refers to the diradical —S(=O)$_2$—.

The terms "sulfonamide", "sulfonamido" and "sulfonamidyl" as used herein, alone or in combination, refer to the diradical groups —S(=O)$_2$—NH— and —NH—S(=O)$_2$—.

The terms "sulfamide", "sulfamido" and "sulfamidyl" as used herein, alone or in combination, refer to the diradical group —NH—S(=O)$_2$—NH—.

The term "reactant," as used herein, refers to a nucleophile or electrophile used to create covalent linkages.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Certain Pharmaceutical Terminology

The term "MEK inhibitor" as used herein refers to a compound that exhibits an IC$_{50}$ with respect to MEK activity, of no more than about 100 µM or not more than about 50 µM, as measured in the Mek1 kinase assay described generally herein below. "IC$_{50}$" is that concentration of inhibitor which reduces the activity of an enzyme (e.g., MEK) to half-maximal level. Compounds described herein have been discovered to exhibit inhibition against MEK. Compounds of the present invention preferably exhibit an IC$_{50}$ with respect to MEK of no more than about 10 µM, more preferably, no more than about 5 µM, even more preferably not more than about 1 µM, and most preferably, not more than about 200 nM, as measured in the Mek1 kinase assay described herein.

The term "treatment" as used herein, is intended to include prophylaxis.

The term "patient" as used herein, is intended to include all mammals including humans. Examples of patients include humans, cows, dogs, cats, goats, sheep, pigs, and rabbits. Preferably, the patient is a human.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutically acceptable derivative or prodrug" as used herein, refers to any pharmaceutically acceptable salt, ester, salt of an ester or other derivative of a compound of formula I, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound of the invention in its free base form with a suitable organic or inorganic acid, and isolating the salt thus formed. Examples of pharmaceutically acceptable salts include those salts prepared by reaction of the compounds of this invention with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts. See, e.g., Berge et al. "Pharmaceutical Salts", *J. Pharm. Sci.* 1977, 66:1-19.

Compounds described herein that contain one or more acidic functional groups are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of some of the bases that can be used include sodium hydroxide, potassium hydroxide, choline hydroxide, sodium carbonate, N$^+$(C$_{1-4}$ alkyl)$_4$, and the like. Representative organic amines useful for the formation of base addition salts include ethylamine, diethylamine, ethylenediamine, ethanolamine, diethanolamine, piperazine and the like. This invention also envisions the quaternization of any basic nitrogen-containing groups of the compounds disclosed herein. Water or oil-soluble or dispersible products may be obtained by such quaternization. See, for example, Berge et al., supra.

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference.

The term "prodrugs" as used herein includes, but is not limited to, the following groups and combinations of these groups:

Amine derived prodrugs:

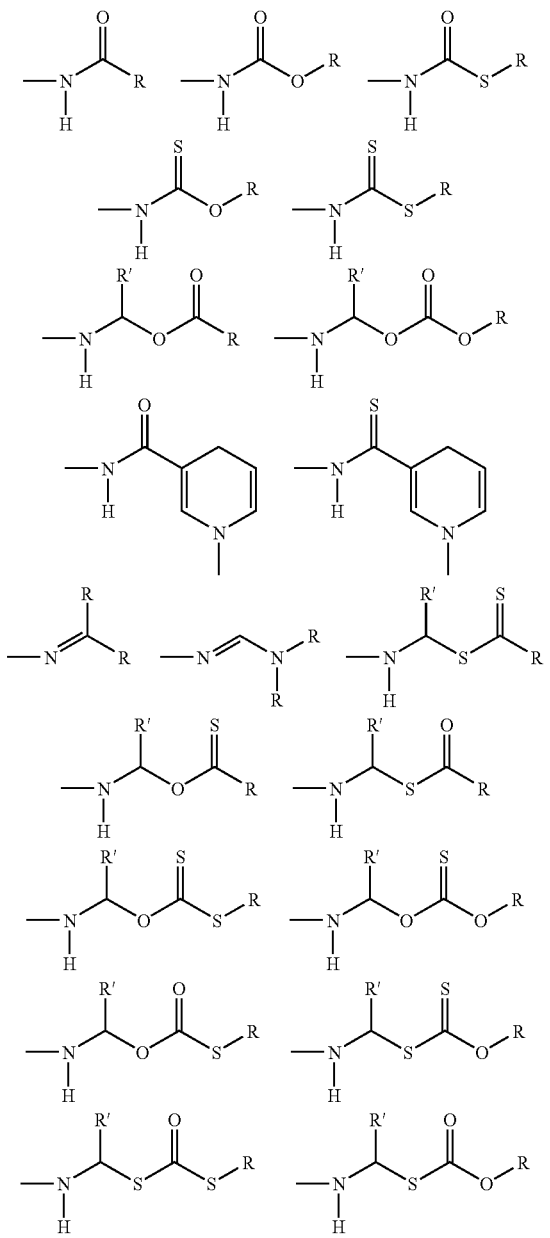

Hydroxy prodrugs include, but are not limited to acyloxyalkyl esters, alkoxycarbonyloxyalkyl esters, alkyl esters, aryl esters and disulfide containing esters.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "carrier" as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount", "therapeutically effective amount" or "pharmaceutically effective amount" as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition," as used herein, refers to a mixture of an active compound with other chemical components, such as carriers, stabilizers, diluents, dispersing agents, suspending agents, thickening agents, and/or excipients.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition.

Compounds

Described herein are compounds of formula I, pharmaceutically acceptable salts, solvates, polymorphs, esters, tautomers or prodrugs thereof,

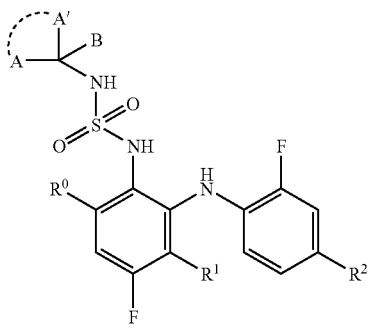

formula I wherein

B is H, $C_1$-$C_4$ alkyl, or $C_2$-$C_6$ alkenyl;
  wherein said $C_1$-$C_4$ alkyl is optionally substituted with one or two hydroxy groups;

A and A' are each independently H, $C_1$-$C_4$ alkyl, or $C_2$-$C_6$ alkenyl;
  wherein said $C_1$-$C_4$ alkyl is optionally substituted with one or two hydroxy groups; or A and A' together with the carbon atom to which they are attached, form a cyclopropyl, cyclobutyl, or cyclopentyl group, optionally substituted with methyl, hydroxy, or halogen;

$R^1$ is H or F;

$R^2$ is Br or I;

$R^0$ is H, halogen, hydroxy, azido, cyano, cyanomethyl or nitro; or $R^0$ is $C_1$-$C_6$ alkyl, $C_3$-$C_6$ cycloalkyl, $C_2$-$C_6$ alkenyl, or $C_2$-$C_6$ alkynyl;
  wherein each alkyl, cycloalkyl, alkenyl, or alkynyl group is optionally substituted with 1-3 substituents selected independently from halogen, hydroxy, azido, cyano, cyanomethyl, nitro, phenyl, difluoromethyl, trifluoromethyl, $C_1$-$C_4$ alkoxy and difluoromethoxy; or $R^0$ is phenyl, optionally substituted with halogen, hydroxy, azido, cyano, cyanomethyl, nitro, phenyl, difluoromethyl, trifluoromethyl, methoxy, $C_1$-$C_4$ alkyl, or $C_1$-$C_4$ alkoxy; or $R^0$ is $OR^3$, O—C(=O)$R^4$, C(=O)$OR^5$, —O—C(O)—$NR^6R^7$, $NR^6R^7$, —$NR^8$C(=O)$NR^9R^{10}$, —$SR^{11}$, NHC(=O)$R^2$, C(=O)$NR^9R^{10}$, $NHSO_2R^{13}$, or $SO_2NR^{14}R^{15}$;
  wherein $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently H, $C_1$-$C_4$ alkyl or phenyl;
    wherein each $C_1$-$C_4$ alkyl or phenyl group is optionally substituted with halogen, hydroxy, azido, cyano, cyanomethyl, nitro, phenyl, difluoromethyl, trifluoromethyl, methoxy, or $C_1$-$C_4$ alkoxy; or $R^0$ is a 5 or 6-atom heterocyclic group, which group may be saturated, unsaturated, or aromatic, containing 1-5 heteroatoms selected independently from O, N, and S, which heterocyclic group is optionally substituted with halogen, hydroxy, azido, cyano, cyanomethyl, nitro, phenyl, difluoromethyl, trifluoromethyl, $C_1$-$C_4$ alkyl, $C_1$-$C_4$ alkoxy or difluoromethoxy; or $R^0$ is a 5- to 10-atom monocyclic or bicyclic heterocyclic group, which group may be saturated, unsaturated, or aromatic, containing 1-5 heteroatoms selected independently from O, N, and S, which heterocyclic group is optionally substituted with halogen, hydroxy, azido, cyano, cyanomethyl, nitro, phenyl, difluoromethyl, trifluoromethyl, $C_1$-$C_4$ alkyl, $C_1$-$C_4$ alkoxy or difluoromethoxy.

In some embodiments, $R^0$ is a 5 or 6-atom heterocyclic group, which group may be saturated, unsaturated, or aromatic, containing 1-5 heteroatoms selected independently from O, N, and S, which heterocyclic group is optionally substituted with $C_1$-$C_4$ alkyl, halogen, hydroxy, or $C_1$-$C_4$ alkoxy.

In further or additional embodiments $R^0$ is isothiazolyl, isoxazolyl, isoxazolinyl, isoxazolidinyl, oxazolyl, oxazolinyl, oxazolidinyl, thiazolyl, triazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, piperidinyl, pyrimidyl, morpholyl, or tetrahydrofuryl, optionally substituted with $C_1$-$C_4$ alkyl, halogen, hydroxy, or $C_1$-$C_4$ alkoxy.

In further or additional embodiments $R^0$ is $C_1$-$C_6$ alkyl, $C_3$-$C_6$ cycloalkyl, $C_2$-$C_6$ alkenyl or $C_2$-$C_6$ alkynyl, wherein each alkyl, cycloalkyl, alkenyl, or alkynyl group is optionally substituted with 1-3 substituents selected independently from halogen, hydroxy, azido, cyano, cyanomethyl, nitro, phenyl, difluoromethyl, trifluoromethyl, $C_1$-$C_4$ alkoxy and difluoromethoxy; or $R^0$ is $OR^3$ or $NR_6R_7$; $R^3$ is $C_1$-$C_4$ alkyl; and $R^6$ and $R^7$ are each independently H, $C_1$-$C_4$ alkyl or phenyl, wherein each $C_1$-$C_4$ alkyl or phenyl group is optionally substituted with halogen, methyl, trifluoromethyl, hydroxy, or alkoxy.

In further or additional embodiments B is —H, —$CH_3$, —$CH_2CH_2OH$, —$CH_2CH(OH)CH_2OH$, —$(CH_2)_2CH(OH)CH_2OH$, —$CH_2$—CH=$CH_2$ or —$CH_2$—$CH_2$CH=$CH_2$; and A and A' are both H; or A and A' together with the carbon atom to which they are attached are

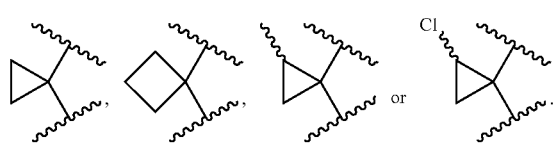

In further or additional embodiments $R^0$ is a 5 or 6-atom heterocyclic group, which group may be saturated, unsaturated, or aromatic, containing 1-5 heteroatoms selected independently from O, N, and S, which heterocyclic group is optionally substituted with $C_1$-$C_4$ alkyl, halogen, hydroxy, or $C_1$-$C_4$ alkoxy; B is —H, —$CH_3$, —$CH_2CH_2OH$, —$CH_2CH(OH)CH_2OH$, —$(CH_2)_2CH(OH)CH_2OH$, —$CH_2$—CH=$CH_2$ or —$CH_2$—$CH_2$CH=$CH_2$; and A and A' are both H; or A and A' together with the carbon atom to which they are attached are

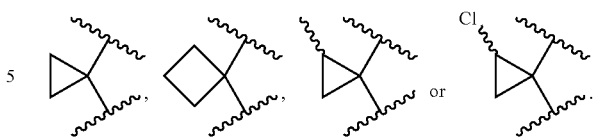

In further or additional embodiments $R^0$ is isothiazolyl, isoxazolyl, isoxazolinyl, isoxazolidinyl, oxazolyl, oxazolinyl, oxazolidinyl, thiazolyl, triazolyl, thienyl, furyl, pyrrolyl, pyrrolinyl, pyrrolidinyl, thiazolinyl, thiazolidinyl, isothiazolinyl, isothiazolidinyl, imidazolinyl, imidazolyl, pyridyl, piperidinyl, pyrimidyl, morpholyl, or tetrahydrofuryl, optionally substituted with $C_1$-$C_4$ alkyl, halogen, hydroxy, or $C_1$-$C_4$ alkoxy; B is —H, —$CH_3$, —$CH_2CH_2OH$, —$CH_2CH(OH)CH_2OH$, —$(CH_2)_2CH(OH)CH_2OH$, —$CH_2$—CH=$CH_2$ or —$CH_2$—$CH_2$CH=$CH_2$; and A and A' are both H; or A and A' together with the carbon atom to which they are attached are

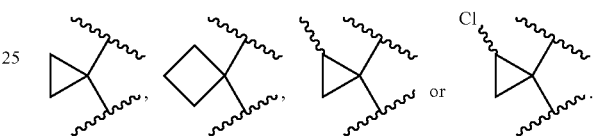

In further or additional embodiments compounds of formula I may be selected from the following table:

| CPD # | —C(A)A'— | —B | $R^0$ | $R^1$ | $R^2$ |
|---|---|---|---|---|---|
| 1 | —$CH_2$— | —H | $OCH_3$ | F | I |
| 2 | —$CH_2$— | —H | $NHCH_3$ | F | I |
| 3 | —$CH_2$— | —H | $CH_2CH_3$ | F | I |
| 4 | —$CH_2$— | —H | $CH_2CH=CH_2$ | F | I |
| 5 | —$CH_2$— | —H | CN | F | I |
| 6 | —$CH_2$— | —H | $CF_3$ | F | I |
| 7 | —$CH_2$— | —H | Cl | F | I |
| 8 | —$CH_2$— | —H | $C_6H_5$ | F | I |
| 9 | —$CH_2$— | —$CH_2CH(OH)CH_2OH$ | $OCH_3$ | F | I |
| 10 | —$CH_2$— | —$CH_2CH(OH)CH_2OH$ | $NHCH_3$ | F | I |
| 11 | —$CH_2$— | —$CH_2CH(OH)CH_2OH$ | $CH_2CH_3$ | F | I |
| 12 | cyclopropyl | —$CH_2$—$CH_2$—CH=$CH_2$ | $OCH_3$ | F | I |
| 13 | cyclopropyl | —$CH_2$—$CH_2$—CH=$CH_2$ | $NHCH_3$ | F | I |
| 14 | cyclopropyl | —$CH_2$—$CH_2$—CH=$CH_2$ | $CH_2CH_3$ | F | I |

-continued

| CPD # | —C(A)A'— | —B | R⁰ | R¹ | R² |
|---|---|---|---|---|---|
| 15 | cyclopropyl | —CH₃ | H | F | I |
| 16 | cyclopropyl | —CH₂CH₂OH | H | F | I |
| 17 | cyclopropyl | —(CH2)₂CH(OH)CH₂OH | H | F | I |
| 18 | CH(CH₃) | —(CH₂)₂CH(OH)CH₂OH | H | F | I |
| 19 | cyclopropyl | —CH₃ | OCH₃ | F | I |
| 20 | cyclopropyl | —CH₂CH₂OH | OCH₃ | F | I |
| 21 | cyclopropyl | —(CH₂)₂CH(OH)CH₂OH | OCH₃ | F | I |
| 22 | CH(CH₃) | —(CH₂)₂CH(OH)CH₂OH | OCH₃ | F | I |
| 23 | cyclopropyl | —CH₃ | CF₃ | F | I |
| 24 | cyclopropyl | —CH₂CH₂OH | CF₃ | F | I |
| 25 | cyclopropyl | —(CH₂)₂CH(OH)CH₂OH | OCH₃ | F | I |

-continued

| CPD # | —C(A)A'— | —B | R⁰ | R¹ | R² |
|---|---|---|---|---|---|
| 26 | Cl-cyclopropyl | —CH₂CH(OH)CH₂OH | OCH₃ | F | I |
| 27 | Cl-cyclopropyl | —H | OCH₃ | F | I |
| 28 | CH₃-cyclopropyl | —H | CH=CH₂ | F | I |
| 29 | cyclobutyl | —CH₂CH(OH)CH₂OH | OCH₃ | F | I |
| 30 | cyclobutyl | —CH₂CH(OH)CH₂OH | NHCH₃ | F | I |
| 31 | cyclobutyl | —CH₂CH(OH)CH₂OH | CH₂CH₃ | F | I |
| 32 | cyclobutyl | —CH₂CH(OH)CH₂OH | CH₂CH=CH₂ | F | I |
| 33 | cyclobutyl | —CH₂CH(OH)CH₂OH | N(CH₃)₂ | F | I |
| 34 | cyclobutyl | —CH₂—CH₂—CH=CH₂ | OCH₃ | F | I |
| 35 | cyclopentyl | —CH₂—CH₂—CH=CH₂ | NHCH₃ | F | I |
| 36 | cyclopentyl | —CH₂—CH₂—CH=CH₂ | CH₂CH₃ | F | I |

-continued

| CPD # | —C(A)A'— | —B | R⁰ | R¹ | R² |
|---|---|---|---|---|---|
| 37 | cyclopentane (spiro) | —CH₃ | CH=CH₂ | F | I |
| 38 | Cl-cyclopentane (spiro) | —CH₂CH₂OH | OCH₃ | F | I |
| 39 | HO-cyclopentane (spiro) | —(CH₂)₂CH(OH)CH₂OH | NHCH₃ | F | I |
| 40 | HO-cyclopentane (spiro) | —CH₃ | OCH₃ | F | I |
| 41 | —CH₂— | —H | OCH₃ | H | I |
| 42 | —CH₂— | —H | NHCH₃ | H | I |
| 43 | —CH₂— | —H | CH₂CH₃ | H | I |
| 44 | —CH₂— | —H | CH₂CH=CH₂ | H | I |
| 45 | —CH₂— | —H | CN | H | Br |
| 46 | —CH₂— | —H | CF₃ | H | Br |
| 47 | —CH₂— | —H | Cl | H | Br |
| 48 | —CH₂— | —H | C₆H₅ | H | Br |
| 49 | —CH₂— | —CH₂CH(OH)CH₂OH | OCH₃ | H | Br |
| 50 | —CH₂— | —CH₂CH(OH)CH₂OH | NHCH₃ | H | Br |
| 51 | —CH₂— | —CH₂CH(OH)CH₂OH | CH₂CH₃ | H | Br |
| 52 | cyclopropane (spiro) | —CH₂—CH₂—CH=CH₂ | OCH₃ | H | I |
| 53 | cyclopropane (spiro) | —CH₂—CH₂—CH=CH₂ | NHCH₃ | H | I |
| 54 | cyclopropane (spiro) | —CH₂—CH₂—CH=CH₂ | CH₂CH₃ | H | I |
| 55 | cyclopropane (spiro) | —CH₃ | 4-imidazolyl | H | I |
| 56 | cyclopropane (spiro) | —CH₂CH₂OH | 4-thiazolyl | H | I |

-continued

| CPD # | —C(A)A'— | —B | R⁰ | R¹ | R² |
|---|---|---|---|---|---|
| 57 | 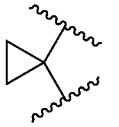 | —(CH₂)₂CH(OH)CH₂OH | 2-oxazolyl | H | I |
| 58 | 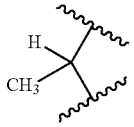 | —(CH₂)₂CH(OH)CH₂OH | 2-furanyl | H | I |
| 59 | 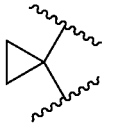 | —CH₃ | OCH₃ | H | Br |
| 60 | 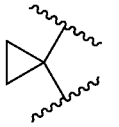 | —CH₂CH₂OH | OCH₃ | H | Br |
| 61 | 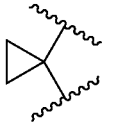 | —(CH₂)₂CH(OH)CH₂OH | OCH₃ | H | Br |
| 62 | 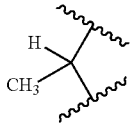 | —(CH₂)₂CH(OH)CH₂OH | OCH₃ | H | Br |
| 63 | —CH₂— | —H | 4-imidazolyl | F | I |
| 64 | —CH₂— | —CH₃ | 4-thiazolyl | F | I |
| 65 | —CH₂— | —CH₂CH₂OH | 2-oxazolyl | F | I |
| 66 | —CH₂— | —(CH₂)₂CH(OH)CH₂OH | 2-furanyl | F | I |
| 67 | —CH₂— | —H | 1,2,3-triazolyl-4-yl | F | I |
| 68 | —CH₂— | —H | 2-thienyl | F | I |
| 69 | —CH₂— | —H | 3-isothiazolyl | F | I |
| 70 | —CH₂— | —H | 4-isothiazolyl | F | I |
| 71 | —CH₂— | —H | 3-isoxazolyl | F | I |
| 72 | 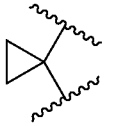 | —CH₃ | 4-imidazolyl | H | Br |
| 73 | 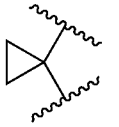 | —CH₂CH₂OH | 4-thiazolyl | H | Br |
| 74 | 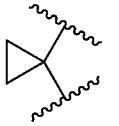 | —(CH₂)₂CH(OH)CH₂OH | 2-oxazolyl | H | Br |

-continued

| CPD # | —C(A)A'— | —B | R⁰ | R¹ | R² |
|---|---|---|---|---|---|
| 75 | (structure) | —(CH$_2$)$_2$CH(OH)CH$_2$OH | 2-furanyl | H | Br |
| 76 | (cyclopropyl structure) | —CH$_3$ | 1,2,3-triazolyl-4-yl | H | Br |
| 77 | (cyclopropyl structure) | —CH$_2$CH$_2$OH | 4-imidazolyl | H | Br |
| 78 | —CH$_2$— | —(CH$_2$)$_2$CH(OH)CH$_2$OH | 3-isothiazolyl | F | Br |
| 79 | —CH$_2$— | —H | 4-isothiazolyl | F | Br |
| 80 | —CH$_2$— | —H | 3-isoxazolyl | F | Br |
| 81 | (cyclopropyl structure) | —CH$_3$ | 4-imidazolyl | F | Br |
| 82 | (cyclopropyl structure) | —CH$_2$CH$_2$OH | 4-thiazolyl | F | Br |
| 83 | (cyclopropyl structure) | —(CH$_2$)$_2$CH(OH)CH$_2$OH | 2-oxazolyl | F | Br |

In a preferred embodiment, the invention provides for compounds of formula I and their pharmaceutically acceptable salts.

In further or additional embodiments, the invention provides for compounds of formula I and their pharmaceutically acceptable solvates.

In further or additional embodiments, the invention provides for compounds of formula I and their pharmaceutically acceptable polymorphs.

In further or additional embodiments, the invention provides for compounds of formula I and their pharmaceutically acceptable esters.

In further or additional embodiments, the invention provides for compounds of formula I and their pharmaceutically acceptable tautomers.

In further or additional embodiments, the invention provides for compounds of formula I and their pharmaceutically acceptable prodrugs.

In further or additional embodiments R⁰ is fused to the ring to which it is attached.

In further or additional embodiments, B is H, C$_1$-C$_4$ alkyl, or C$_2$-C$_6$ alkenyl, wherein said C$_2$-C$_6$ alkenyl is optionally substituted with one or two hydroxy groups.

In further or additional embodiments, A and A' are each independently H, C$_1$-C$_4$ alkyl, or C$_2$-C$_6$ alkenyl, wherein said C$_2$-C$_6$ alkenyl is optionally substituted with one or two hydroxy groups.

In further or additional embodiments, R¹ is H, fluoro, chloro, bromo or iodo.

In further or additional embodiments, R² is H, fluoro, chloro, bromo or iodo.

In addition to the definitions given above for the groups A, A', B, R⁰, R¹, R², R³, R⁴, R⁵, R⁶, R⁷, R⁸, R⁹, R¹⁰, R¹¹, R¹², R¹³, R¹⁴ and R¹⁵ additional substitutions which could be contemplated by those of skill in the chemical and pharmaceutical arts are included.

In further or additional embodiments are compounds of formula IA, pharmaceutically acceptable salts, solvates, polymorphs, esters, tautomers or prodrugs thereof,

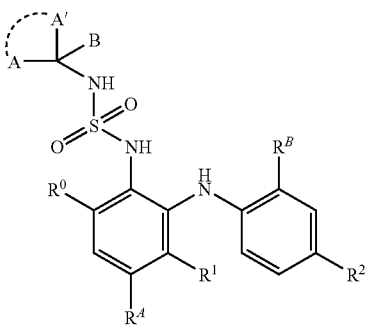

formula I$_A$ wherein

B is H, $C_1$-$C_4$ alkyl, or $C_2$-$C_6$ alkenyl;
  wherein said $C_1$-$C_4$ alkyl is optionally substituted with one or two hydroxy groups;

A and A' are each independently H, $C_1$-$C_4$ alkyl, or $C_2$-$C_6$ alkenyl;
  wherein said $C_1$-$C_4$ alkyl is optionally substituted with one or two hydroxy groups; or A and A' together with the carbon atom to which they are attached, form a cyclopropyl, cyclobutyl, or cyclopentyl group, optionally substituted with methyl, hydroxy, or halogen;

$R^1$, $R^2$, $R^A$ and $R^B$ are each independently H, fluoro, chloro, bromo or iodo;

$R^0$ is H, halogen, hydroxy, azido, cyano, cyanomethyl or nitro; or $R^0$ is $C_1$-$C_6$ alkyl, $C_3$-$C_6$ cycloalkyl, $C_2$-$C_6$ alkenyl, or $C_2$-$C_6$ alkynyl;
  wherein each alkyl, cycloalkyl, alkenyl, or alkynyl group is optionally substituted with 1-3 substituents selected independently from halogen, hydroxy, azido, cyano, cyanomethyl, nitro, phenyl, difluoromethyl, trifluoromethyl, $C_1$-$C_4$ alkoxy and difluoromethoxy; or $R^0$ is phenyl, optionally substituted with halogen, hydroxy, azido, cyano, cyanomethyl, nitro, phenyl, difluoromethyl, trifluoromethyl, methoxy, $C_1$-$C_4$ alkyl, or $C_1$-$C_4$ alkoxy; or $R^0$ is $OR^3$, O—C(=O)$R^4$, C(=O)$OR^5$, —O—C(O)—$NR^6R^7$, $NR^6R^7$, —$NR^8$C(=O)$NR^9R^{10}$, —$SR^{11}$, NHC(=O)$R^{12}$, C(=O)$NR^9R^{10}$, $NHSO_2R^{13}$, or $SO_2NR^{14}R^{15}$;
  wherein $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are each independently H, $C_1$-$C_4$ alkyl or phenyl;
    wherein each $C_1$-$C_4$ alkyl or phenyl group is optionally substituted with halogen, hydroxy, azido, cyano, cyanomethyl, nitro, phenyl, difluoromethyl, trifluoromethyl, methoxy, or $C_1$-$C_4$ alkoxy; or $R^0$ is a 5 or 6-atom heterocyclic group, which group may be saturated, unsaturated, or aromatic, containing 1-5 heteroatoms selected independently from O, N, and S, which heterocyclic group is optionally substituted with halogen, hydroxy, azido, cyano, cyanomethyl, nitro, phenyl, difluoromethyl, trifluoromethyl, $C_1$-$C_4$ alkyl, $C_1$-$C_4$ alkoxy or difluoromethoxy; or $R^0$ is a 5- to 10-atom monocyclic or bicyclic heterocyclic group, which group may be saturated, unsaturated, or aromatic, containing 1-5 heteroatoms selected independently from O, N, and S, which heterocyclic group is optionally substituted with halogen, hydroxy, azido, cyano, cyanomethyl, nitro, phenyl, difluoromethyl, trifluoromethyl, $C_1$-$C_4$ alkyl, $C_1$-$C_4$ alkoxy or difluoromethoxy.

Compounds of formula I, pharmaceutically acceptable salts, pharmaceutically active metabolites, pharmaceutically acceptable prodrugs, and pharmaceutically acceptable solvates thereof, may modulate the activity of MEK enzymes; and, as such, are useful for treating diseases or conditions in which aberrant MEK enzyme activity contributes to the pathology and/or symptoms of a disease or condition.

Also described herein are prodrugs of compounds of formula I and methods of treating disorders. For example, the invention provides for methods of treating proliferative disorders, or abnormal cell growth, by administering prodrugs of compounds of formula I. The prodrugs of compounds of formula I can be administered as pharmaceutical compositions. Compounds of formula I having free amino, amido, hydroxy or carboxylic groups can be converted into prodrugs.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. Additional types of prodrugs are also encompassed.

For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews* 1996, 19, 115. Carbamate prodrugs of hydroxy and amino groups are also included, as are carbonate prodrugs, sulfonate esters and sulfate esters of hydroxy groups.

Derivatization of hydroxy groups as (acyloxy) methyl and (acyloxy) ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

Described herein are pharmaceutical compositions. In some embodiments the invention provides pharmaceutical compositions for the treatment of disorders such as hyperproliferative disorder in a mammal. In some embodiments, the treatment of said disorders comprises a therapeutically effective amount of a compound formula I, or a pharmaceutically acceptable salt, ester, prodrug, solvate, hydrate or derivative thereof, and a pharmaceutically acceptable carrier. In some embodiments, said pharmaceutical composition is for the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

Also described are pharmaceutical compositions for the treatment of pancreatitis or kidney disease (including proliferative glomerulonephritis and diabetes-induced renal disease) or pain in a mammal which comprises a therapeutically effective amount of a compound of formula I, or a pharmaceutically acceptable salt, ester, prodrug, solvate, hydrate or derivative thereof, and a pharmaceutically acceptable carrier.

Also described are pharmaceutical compositions for the prevention of blastocyte implantation in a mammal which comprises a therapeutically effective amount of a compound of formula I, or a pharmaceutically acceptable salt, ester, prodrug, solvate, hydrate or derivative thereof, and a pharmaceutically acceptable carrier.

Also described are pharmaceutical compositions for treating a disease related to vasculogenesis or angiogenesis in a mammal which comprises a therapeutically effective amount of a compound formula I, or a pharmaceutically acceptable salt, ester, prodrug, solvate, hydrate or derivative thereof, and a pharmaceutically acceptable carrier. In some embodiments, said pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Methods of Treatment

Also described are methods of treating a disease in an individual suffering from said disease comprising administering to said individual an effective amount of a composition comprising a compound of formula I or a pharmaceutically acceptable salt, solvate, polymorph, ester, tautomer or prodrug thereof.

Also described are methods of treating a hyperproliferative disorder in a mammal that comprise administering to said mammal a therapeutically effective amount of a compound of formula I, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

Also described are methods for the treatment of a hyperproliferative disorder in a mammal that comprise administering to said mammal a therapeutically effective amount of a compound of formula I, or a pharmaceutically acceptable salt, ester, prodrug, solvate, hydrate or derivative thereof, in combination with an anti-tumor agent. In some embodiments, the anti-tumor agent is selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

Also described are methods of treating pancreatitis or kidney disease or pain in a mammal that comprise administering to said mammal a therapeutically effective amount of a compound formula I, or a pharmaceutically acceptable salt, ester, prodrug, solvate, hydrate or derivative thereof.

Also described are methods of preventing blastocyte implantation in a mammal that comprises administering to said mammal a therapeutically effective amount of a compound of formula I, or a pharmaceutically acceptable salt, ester, prodrug, solvate, hydrate or derivative thereof.

Also described are methods of treating diseases related to vasculogenesis or angiogenesis in a mammal that comprise administering to said mammal a therapeutically effective amount of a compound of formula I, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with the compounds described herein, or a pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, and myeloproliferative disorders; bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/ lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer Also described are methods of modulating MEK activity by contacting MEK with an amount of a compound of formula I sufficient to modulate the activity of MEK. Modulate can be inhibiting or activating MEK activity. In some embodiments, the invention provides methods of inhibiting MEK activity by contacting MEK with an amount of a compound of formula I sufficient to inhibit the activity of MEK. In some embodiments, the invention provides methods of inhibiting MEK activity in a solution by contacting said solution with an amount of a compound of formula I sufficient to inhibit the activity of MEK in said solution. In some embodiments, the invention provides methods of inhibiting MEK activity in a cell by contacting said cell with an amount of a compound of the invention sufficient to inhibit the activity of MEK in said cell. In some embodiments, the invention provides methods of inhibiting MEK activity in a tissue by contacting said tissue with an amount of a compound of the invention sufficient to inhibit the activity of MEK in said tissue. In some embodiments, the invention provides methods of inhibiting MEK activity in an organism by contacting said organism with an amount of a compound of formula I sufficient to inhibit the activity of MEK in said organism. In some embodiments, the invention provides methods of inhibiting MEK activity in an animal by contacting said animal with an amount of a compound of formula I sufficient to inhibit the activity of MEK in said animal. In some embodiments, the invention provides methods of inhibiting MEK activity in a mammal by contacting said mammal with an amount of a compound of formula I sufficient to inhibit the activity of MEK in said mammal. In some embodiments, the invention provides methods of inhibiting MEK activity in a human by contacting said humal with an amount of a compound of formula I sufficient to inhibit the activity of MEK in said human.

Also described are pharmaceutical compositions for inhibiting abnormal cell growth in a mammal which comprise an amount of a compound of formula I, or a pharmaceutically acceptable salt, ester, prodrug, solvate, hydrate or derivative thereof, in combination with an amount of a chemotherapeutic, wherein the amounts of the compound, salt, ester, prodrug, solvate, hydrate or derivative, and of the chemotherapeutic are together effective in inhibiting abnormal cell growth. Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Also described are methods for inhibiting abnormal cell growth in a mammal or treating a hyperproliferative disorder which comprise administering to the mammal an amount of a compound of formula I, or a pharmaceutically acceptable salt, ester, prodrug, solvate, hydrate or derivative thereof, in combination with radiation therapy, wherein the amounts of the compound, salt, ester, prodrug, solvate, hydrate or derivative, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of formula I in this combination therapy can be determined as described herein.

The invention also relates to a method of and to a pharmaceutical composition of inhibiting abnormal cell growth in a mammal which comprises an amount of a compound of formula I, or a pharmaceutically acceptable salt, ester, prodrug, solvate, hydrate or derivative thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The term "treating" and its grammatical equivalents as used herein include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

In some embodiments the compounds of formula I will be co-administered with other agents as described above. The term "Co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present. Thus, in some embodiments, the compounds of the invention and the other agent(s) are administered in a single composition. In some embodiments, compounds of the invention and the other agent(s) are admixed in the composition.

Synthetic Procedures

In another aspect, methods for synthesizing the compounds described herein are provided. In some embodiments, the compounds described herein can be prepared by the methods described below. The procedures and examples below are intended to illustrate those methods. Neither the procedures nor the examples should be construed as limiting the invention in any way. Compounds of formula I may also be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting materials used for the synthesis of the compounds of formula I as described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles or nucleophiles to form new functional groups or substituents. The table below entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

| Covalent Linkage Product | Electrophile | Nucleophile |
| --- | --- | --- |
| Carboxamides | Activated esters | Amines/anilines |
| Carboxamides | Acyl azides | Amines/anilines |
| Carboxamides | Acyl halides | Amines/anilines |
| Esters | Acyl halides | Alcohols/phenols |
| Esters | Acyl nitriles | Alcohols/phenols |
| Carboxamides | Acyl nitriles | Amines/anilines |
| Imines | Aldehydes | Amines/anilines |
| Hydrazones | Aldehydes or ketones | Hydrazines |
| Oximes | Aldehydes or ketones | Hydroxylamines |
| Alkyl amines | Alkyl halides | Amines/anilines |
| Esters | Alkyl halides | Carboxylic acids |
| Thioethers | Alkyl halides | Thiols |
| Ethers | Alkyl halides | Alcohols/phenols |
| Thioethers | Alkyl sulfonates | Thiols |
| Esters | Alkyl sulfonates | Carboxylic acids |
| Ethers | Alkyl sulfonates | Alcohols/phenols |
| Esters | Anhydrides | Alcohols/phenols |
| Carboxamides | Anhydrides | Amines/anilines |
| Thiophenols | Aryl halides | Thiols |
| Aryl amines | Aryl halides | Amines |
| Thioethers | Azindines | Thiols |
| Boronate esters | Boronates | Glycols |
| Carboxamides | Carboxylic acids | Amines/anilines |
| Esters | Carboxylic acids | Alcohols |
| Hydrazines | Hydrazides | Carboxylic acids |
| N-acylureas or Anhydrides | Carbodiimides | Carboxylic acids |
| Esters | Diazoalkanes | Carboxylic acids |
| Thioethers | Epoxides | Thiols |
| Thioethers | Haloacetamides | Thiols |
| Ammotriazines | Halotriazines | Amines/anilines |
| Triazinyl ethers | Halotriazines | Alcohols/phenols |
| Amidines | Imido esters | Amines/anilines |
| Ureas | Isocyanates | Amines/anilines |
| Urethanes | Isocyanates | Alcohols/phenols |
| Thioureas | Isothiocyanates | Amines/anilines |
| Thioethers | Maleimides | Thiols |
| Phosphite esters | Phosphoramidites | Alcohols |
| Silyl ethers | Silyl halides | Alcohols |
| Alkyl amines | Sulfonate esters | Amines/anilines |
| Thioethers | Sulfonate esters | Thiols |
| Esters | Sulfonate esters | Carboxylic acids |
| Ethers | Sulfonate esters | Alcohols |
| Sulfonamides | Sulfonyl halides | Amines/anilines |
| Sulfonate esters | Sulfonyl halides | Phenols/alcohols |

Examples of Covalent Linkages and Precursors Thereof

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a $Pd_0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Protecting or blocking groups may be selected from:

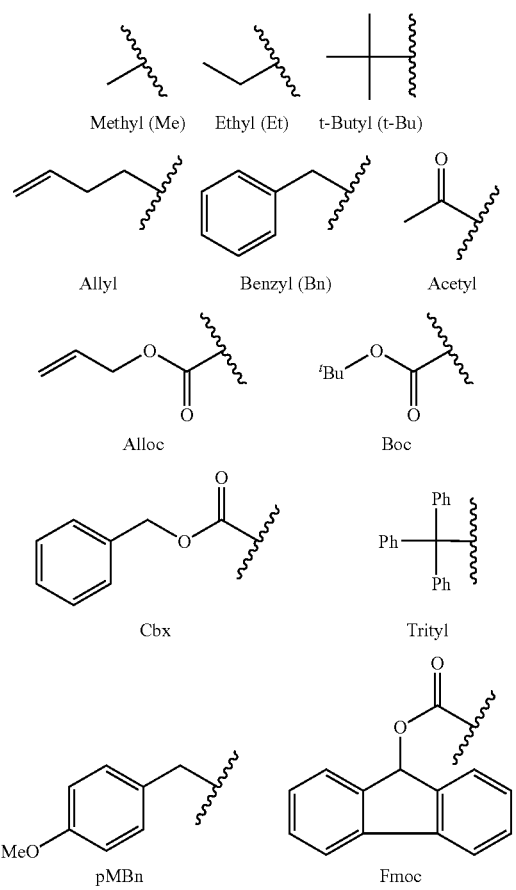

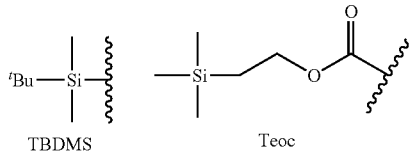

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference in their entirety.

Preparing Compounds of Formula I

Described herein are processes for the preparation of compounds of formula (I), which can be synthesized according to the reaction scheme below:

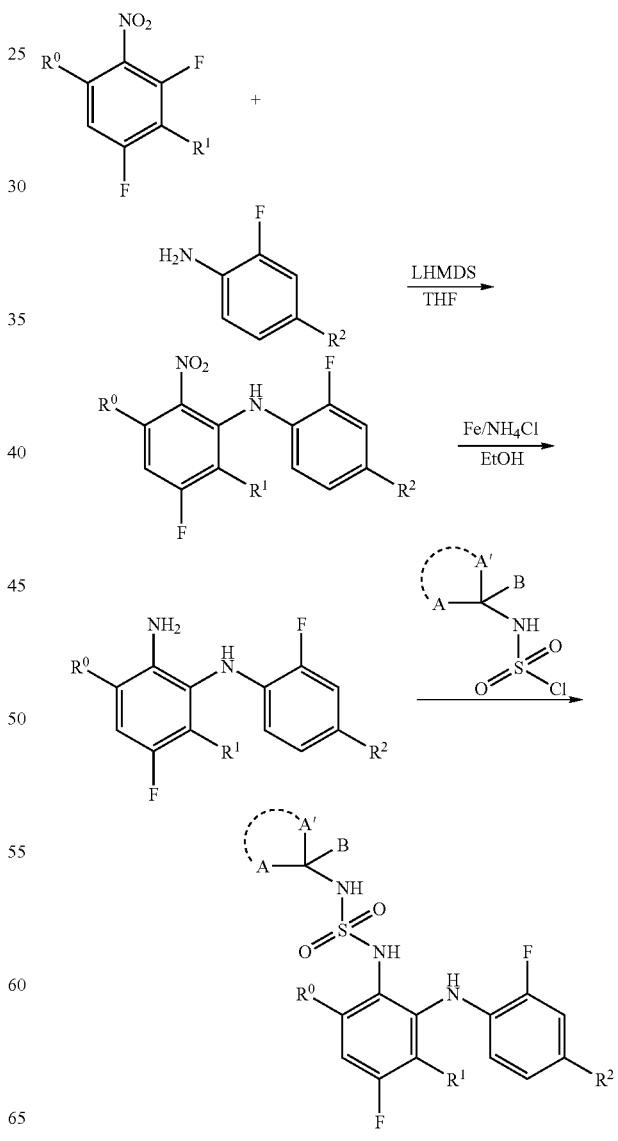

General Procedures for the Synthesis of Compounds of Formula I

Preparation of (2-Fluoro-4-$R^2$-phenyl)-(2-$R^1$-3-fluoro-5-$R^0$-6-nitro-phenyl)amines

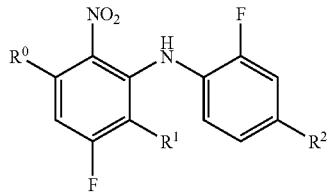

2-Fluoro-4-$R^2$-aniline (1 eq) and lithium hexamethyl disilazide (LiN(SiMe$_3$)$_2$; LHMDS, 1 eq) are reacted in dry THF at −78° C. After stirring at −78° C. for one hour, 2,4-difluoro-3-$R^1$-5-$R^0$-nitrobenzene is added. The reaction mixture is allowed to warm to room temperature and stirring continued for a further 16 hours. Ethyl acetate (200 mL) is added and the mixture washed with water. The organic phase is dried over sodium sulfate and purified by column chromatography.

Preparation of 3-$R^9$-6-$R^1$-5-Fluoro-N1-(2-Fluoro-4-$R^2$-phenyl)-benzene-1,2-diamine

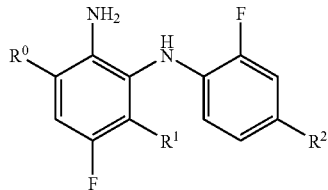

Ammonium chloride and iron powder are added to a stirred solution of (2-Fluoro-4-$R^2$-phenyl)-(2-$R^1$-3-fluoro-5-$R^0$-6-nitro-phenyl)amine (1.34 mmol) in ethanol and heated at reflux for 16 hours. After cooling the reaction mixture is filtered over celite and concentrated to dryness. The residue obtained is dissolved in ethyl acetate and washed with water. The organic phase is dried over sodium sulfate and purified by crystallization from ethanol.

Preparation of Sulfonamidyl Chlorides

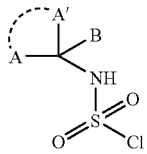

A solution of amine (AA'C(B)—NH$_2$) and DMAP in dry dichloromethane is added to a solution of sulfuryl chloride (SO$_2$Cl$_2$) in dry dichloromethane at −78° C. (acetone/dry-ice bath). The resulting mixture is maintained at −50° C. for 1 hr; then the bath is removed and stirring continued for 2 hrs. The crude reaction product is used in the next reaction without workup.

Coupling Anilines with Sulfonamidyl Chlorides

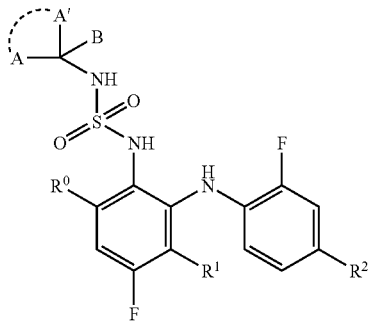

Sulfonamidyl chloride (AA'C(B)—NH—SO$_2$—Cl) is added dropwise to a solution of aniline (prepared as described above) in dry pyridine at −10° C. The mixture is allowed to warm to room temperature and stirred for a further 16 hrs. Water is added and the mixture washed with HCl (1N) and extracted with ethyl acetate. The combined organic layers are dried over MgSO$_4$ and concentrated. The product may be purified or used without further purification in any subsequent reactions.

Further Forms of Compounds of Formula I

Isomers of Compounds of Formula I

The compounds described herein may exist as geometric isomers. The compounds described herein may possess one or more double bonds. The compounds presented herein include all cis, trans, syn, anti, entgegen (E), and zusammen (Z) isomers as well as the corresponding mixtures thereof. In some situations, compounds may exist as tautomers. The compounds described herein include all possible tautomers within the formulas described herein. The compounds of formula I may possess one or more chiral centers and each center may exist in the R or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion may also be useful for the applications described herein. Compounds of formula I can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds described herein, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981, herein incorporated by reference in its entirety.

Labeled Compounds of Formula I

Compounds of formula I also include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{37}P$, $^{35}S$, $^{18}F$, and $^{36}Cl$, respectively. Compounds described herein, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds of formula I, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds, pharmaceutically acceptable salt, ester, prodrug, solvate, hydrate or derivative thereof can generally be prepared by carrying out procedures described herein, by substituting a readily available isotopically labeled reagent for a non-isotopically labeled reagent.

The compounds described herein may be labeled by other means, including, but not limited to, the use of chromophores or fluorescent moieties, bioluminescent labels, or chemiluminescent labels.

Pharmaceutically Acceptable Salts of Compounds of Formula I

Compounds of formula I can be prepared as a pharmaceutically acceptable salts formed when an acidic proton present in the parent compound either is replaced by a metal ion, for example an alkali metal ion, an alkaline earth ion, or an aluminum ion; or coordinates with an organic base. In addition, the salt forms of the disclosed compounds can be prepared using salts of the starting materials or intermediates.

Compounds of formula I can be prepared as a pharmaceutically acceptable acid addition salt (which is a type of a pharmaceutically acceptable salt) by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Alternatively, compounds of formula I can be prepared as a pharmaceutically acceptable base addition salts (which is a type of a pharmaceutically acceptable salt) by reacting the free acid form of the compound with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like.

Solvates of Compounds of Formula I

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds of formula I can be conveniently prepared or formed during the processes described herein. By way of example only, hydrates of compounds of formula I can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs of Compounds of Formula I

Compounds of formula I include crystalline forms, also known as polymorphs. Polymorphs include the different crystal packing arrangements of the same elemental composition of a compound. Polymorphs may have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Prodrugs of Compounds of Formula I

Compounds of formula I can be prepared as prodrugs. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of formula I which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety.

Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Additionally, prodrug derivatives of compounds of formula I can be prepared by methods known to those of ordinary skill in the art (e.g., for further details see Saulnier et al., (1994), Bioorganic and Medicinal Chemistry Letters, Vol. 4, p. 1985). By way of example only, appropriate prodrugs can be prepared by reacting a non-derivatized compound of formula I with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds may be a prodrug for another derivative or active compound.

Sites on the aromatic ring portion of compounds of formula I may be susceptible to various metabolic reactions, therefore incorporation of appropriate substituents on the aromatic ring structures, can reduce, minimize or eliminate this metabolic pathway.

Modes of Administration

Described herein are compounds of formula I or a pharmaceutically acceptable salt, solvate, polymorph, ester, tautomer or prodrug thereof. Also described, are pharmaceutical compositions comprising a compound of formula I or a pharmaceutically acceptable salt, solvate, polymorph, ester, tautomer or prodrug thereof.

The compounds and compositions described herein may be administered either alone or in combination with pharmaceutically acceptable carriers, excipients or diluents, in a pharmaceutical composition, according to standard pharmaceutical practice.

Administration of the compounds and compositions described herein can be effected by any method that enables delivery of the compounds to the site of action. These methods include oral routes, intraduodenal routes, parenteral injection (including intravenous, subcutaneous, intraperitoneal, intramuscular, intravascular or infusion), topical, and rectal administration. For example, compounds described herein can be administered locally to the area in need of treatment. This may be achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. The administration can also be by direct injection at the site (or former site) of a tumor or neoplastic or preneoplastic tissue. Those of ordinary skill in the art are familiar with formulation and administration techniques that can be employed with the compounds and methods of the invention, e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

Pharmaceutical preparations may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical preparations may also be formulated in rectal compositions such as suppositories or retention enemas, e.g., containing conventional suppository bases such as cocoa butter, polyethylene glycol, or other glycerides.

Pharmaceutical preparations may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Pharmaceutical preparations for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Formulations

The compounds or compositions described herein can be delivered in a vesicle, e.g., a liposome (see, for example, Langer, *Science* 1990, 249, 1527-1533; Treat et al., *Liposomes in the Therapy of Infectious Disease and Cancer*, Lopez-Bernstein and Fidler, Ed., Liss, N.Y., pp. 353-365, 1989). The compounds and pharmaceutical compositions described herein can also be delivered in a controlled release system. In one embodiment, a pump may be used (see, Sefton, 1987, CRC Crit. Ref. Biomed. Eng. 14:201; Buchwald et al. Surgery, 1980 88, 507; Saudek et al. *N. Engl. J. Med.* 1989, 321, (574). Additionally, a controlled release system can be placed in proximity of the therapeutic target. (See, Goodson, *Medical Applications of Controlled Release*, 1984, Vol. 2, pp. 115-138). The pharmaceutical compositions described herein can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

Pharmaceutical compositions may be in the form of a sterile injectable aqueous solution. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion. The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutical compositions may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a compound or composition of the invention can be used. As used herein, topical application can include mouth washes and gargles.

Pharmaceutical compositions may be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. Preferably, the pharmaceutical composition is in unit dosage form. In such form, the preparation is subdivided into unit doses containing appropriate quantities of the active component, e.g., an effective amount to achieve the desired purpose. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. The amount and frequency of administration of the compounds described herein, and if applicable other therapeutic agents and/or therapies, will be regulated according to the judgment of the attending clinician (physician) considering such factors as described above. Thus the amount of compound of formula I to be administered may vary widely. Administration, may occur in an amount of between about 0.001 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 7000 mg of compound, and preferably includes, e.g., from about 0.05 mg to about 2500 mg. The quantity of active compound in a unit dose of preparation may be varied or adjusted from about 0.1 mg to 1000 mg, preferably from about 1 mg to 300 mg, more preferably 10 mg to 200 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. The amount administered will vary depending on the particular $IC_{50}$ value of the compound used. In combinational applications in which the compound is not the sole therapy, it may be possible to administer lesser amounts of compound and still have therapeutic or prophylactic effect.

Dosage Forms

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 18th Edition (1990).

Combination Therapies

The compounds described herein or a pharmaceutically acceptable salt, solvate, polymorph, ester, tautomer or prodrug thereof may be administered as a sole therapy. The compounds described herein or a pharmaceutically acceptable salt, solvate, polymorph, ester, tautomer or prodrug thereof may also be administered in combination with another therapy or therapies.

By way of example only, if one of the side effects experienced by a patient upon receiving one of the compounds described herein is hypertension, then it may be appropriate to administer an anti-hypertensive agent in combination with the compound. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Other therapies include, but are not limited to administration of other therapeutic agents, radiation therapy or both. In the instances where the compounds described herein are administered with other therapeutic agents, the compounds described herein need not be administered in the same pharmaceutical composition as other therapeutic agents, and may, because of different physical and chemical characteristics, be administered by a different route. For example, the compounds/compositions may be administered orally to generate and maintain good blood levels thereof, while the other therapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician. The particular choice of compound (and where appropriate, other therapeutic agent and/or radiation) will depend upon the diagnosis of the attending physicians and their judgment of the condition of the patient and the appropriate treatment protocol. Other therapeutic agents may include chemotherapeutic agents, such as anti-tumor substances, for example those selected from, mitotic inhibitors, for example vinblastine; alkylating agents, for example cis-platin, carboplatin and cyclophosphamide; anti-metabolites, for example 5-fluorouracil, cytosine arabinside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of treatment.

The compounds and compositions described herein (and where appropriate chemotherapeutic agent and/or radiation) may be administered concurrently (e.g., simultaneously, essentially simultaneously or within the same treatment protocol) or sequentially, depending upon the nature of the disease, the condition of the patient, and the actual choice of chemotherapeutic agent and/or radiation to be administered in conjunction (i.e., within a single treatment protocol) with the compound/composition.

In combinational applications and uses, the compound/composition and the chemotherapeutic agent and/or radiation need not be administered simultaneously or essentially simultaneously, and the initial order of administration of the compound/composition, and the chemotherapeutic agent and/or radiation, may not be important. Thus, the compounds/compositions of the invention may be administered first followed by the administration of the chemotherapeutic agent and/or radiation; or the chemotherapeutic agent and/or radiation may be administered first followed by the administration of the compounds/compositions of the invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the compounds/compositions of the invention followed, where determined advantageous, by the administration of the chemotherapeutic agent and/or radiation, and so on until the treatment protocol is complete. Thus, in accordance with experience and knowledge, the practicing physician can modify each protocol for the administration of a compound/composition for treatment according to the individual patient's needs, as the treatment proceeds. The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Specific, non-limiting examples of possible combination therapies include use of the compounds of the invention with agents found in the following pharmacotherapeutic classifications as indicated below. These lists should not be construed to be closed, but should instead serve as illustrative examples common to the relevant therapeutic area at present. Moreover, combination regimens may include a variety of routes of administration and should include oral, intravenous, intraocular, subcutaneous, dermal, and inhaled topical.

For the treatment of oncologic diseases, proliferative disorders, and cancers, compounds according to the present invention may be administered with an agent selected from the group comprising: aromatase inhibitors, antiestrogen, anti-androgen, corticosteroids, gonadorelin agonists, topoisomerase 1 and 2 inhibitors, microtubule active agents, alkylating agents, nitrosoureas, antineoplastic antimetabolites, platinum containing compounds, lipid or protein kinase targeting agents, IMiDs, protein or lipid phosphatase targeting agents, anti-angiogenic agents, Akt inhibitors, IGF-1 inhibitors, FGF3 modulators, mTOR inhibitors, Smac mimetics, HDAC inhibitors, agents that induce cell differentiation, bradykinin 1 receptor antagonists, angiotensin II antagonists, cyclooxygenase inhibitors, heparanase inhibitors, lymphokine inhibitors, cytokine inhibitors, IKK inhibitors, P38MAPK inhibitors, HSP90 inhibitors, multlikinase inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors, and aminopeptidase inhibitors.

For the treatment of oncologic diseases, proliferative disorders, and cancers, compounds according to the present invention may be administered with an agent selected from the group comprising: dacarbazine (DTIC), actinomycins $C_2$, $C_3$, D, and $F_1$, cyclophosphamide, melphalan, estramustine, maytansinol, rifamycin, streptovaricin, doxorubicin, daunorubicin, epirubicin, idarubicin, detorubicin, carminomycin, idarubicin, epirubicin, esorubicin, mitoxantrone, bleomycins A, $A_2$, and B, camptothecin, Irinotecan®, Topotecan®, 9-aminocamptothecin, 10,11-methylenedioxycamptothecin, 9-nitrocamptothecin, bortezormib, temozolomide, TAS103, NPI0052, combretastatin, combretastatin A-2, combretastatin A-4, calicheamicins, neocarcinostatins, epothilones A B, C, and semi-synthetic variants, Herceptin®, Rituxan®, CD40 antibodies, asparaginase, interleukins, interferons, leuprolide, and pegaspargase, 5-fluorouracil, fluorodeoxyuridine, ptorafur, 5'-deoxyfluorouridine, UFT, MITC, S-1 capecitabine, diethylstilbestrol, tamoxifen, toremefine, tolmudex, thymitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-DACH, ormaplatin, thalidomide, lenalidomide, CI-973, telomestatin, CHIR258, Rad 001, SAHA, Tubacin, 17-AAG, sorafenib, JM-216, podophyllotoxin, epipodophyllotoxin, etoposide, teniposide, Tarceva®, Iressa®, Imatinib®, Miltefosine®, Perifosine®, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and docetaxel.

For the treatment of inflammatory diseases and pain, compounds according to the present invention may be administered with an agent selected from the group comprising: corticosteroids, non-steroidal anti-inflammatories, muscle relaxants and combinations thereof with other agents, anaesthetics and combinations thereof with other agents, expectorants and combinations thereof with other agents, antidepressants, anticonvulsants and combinations thereof; antihypertensives, opioids, topical cannabinoids, and other agents, such as capsaicin.

For the treatment of inflammatory diseases and pain, compounds according to the present invention may be administered with an agent selected from the group comprising: betamethasone dipropionate (augmented and non-augemnted), betamethasone valerate, clobetasol propionate, prednisone, methyl prednisolone, diflorasone diacetate, halobetasol propionate, amcinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, celecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-D-glucose, prilocalne, EMLA Cream (Eutectic Mixture of Local Anesthetics (lidocaine 2.5% and prilocalne 2.5%), guaifenesin, guaifenesin/ketoprofen/cyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentin/clonidine, gabapentin/carbamazepine, carbamazepine/cyclobenzaprine, antihypertensives including clonidine, codeine, loperamide, tramadol, morphine, fentanyl, oxycodone, hydrocodone, levorphanol, butorphanol, menthol, oil of wintergreen, camphor, eucalyptus oil, turpentine oil; CB1/CB2 ligands, acetaminophen, infliximab; n) nitric oxide synthase inhibitors, particularly inhibitors of inducible nitric oxide synthase; and other agents, such as capsaicin.

For the treatment of ophthalmologic disorders and diseases of the eye, compounds according to the present invention may be administered with an agent selected from the group comprising: beta-blockers, carbonic anhydrase inhibitors, alpha.- and .beta.-adrenergic antagonists including a1-adrenergic antagonists, .alpha.2 agonists, miotics, prostaglandin analogs, corticosteroids, and immunosuppressant agents.

For the treatment of ophthalmologic disorders and diseases of the eye, compounds according to the present invention may be administered with an agent selected from the group comprising: timolol, betaxolol, levobetaxolol, carteolol, levobunolol, propranolol, brinzolamide, dorzolamide, nipradilol, iopidine, brimonidine, pilocarpine, epinephrine, latanoprost, travoprost, bimatoprost, unoprostone, dexamethasone, prednisone, methylprednisolone, azathioprine, cyclosporine, and immunoglobulins.

For the treatment of autoimmune disorders, compounds according to the present invention may be administered with an agent selected from the group comprising: corticosteroids, immunosuppressants, prostaglandin analogs and antimetabolites.

For the treatment of autoimmune disorders, compounds according to the present invention may be administered with an agent selected from the group comprising: dexamethasome, prednisone, methylprednisolone, azathioprine, cyclosporine, immunoglobulins, latanoprost, travoprost, bimatoprost, unoprostone, infliximab, rutuximab and methotrexate.

For the treatment of metabolic disorders, compounds according to the present invention may be administered with an agent selected from the group comprising: insulin, insulin derivatives and mimetics, insulin secretagogues, insulin sensitizers, biguanide agents, alpha-glucosidase inhibitors, insulinotropic sulfonylurea receptor ligands, protein tyrosine phosphatase-1B (PTP-1B) inhibitors, GSK3 (glycogen synthase kinase-3) inhibitors, GLP-1 (glucagon like peptide-1), GLP-1 analogs, DPPIV (dipeptidyl peptidase IV) inhibitors, RXR ligands sodium-dependent glucose co-transporter inhibitors, glycogen phosphorylase A inhibitors, an AGE breaker, PPAR modulators, and non-glitazone type PPARS agonist.

For the treatment of metabolic disorders, compounds according to the present invention may be administered with an agent selected from the group comprising: insulin, metformin, Glipizide, glyburide, Amaryl, meglitinides, nateglinide, repaglinide, PT-112, SB-517955, SB4195052, SB-216763, NN-57-05441, NN-57-05445, GW-0791, AGN-.sup.194.sup.204, T-1095, BAY R3401, acarbose Exendin-4, DPP728, LAF237, vildagliptin, MK-0431, saxagliptin, GSK23A, pioglitazone, rosiglitazone, (R)-1-{4-[5-methyl-2-(4-trifluoromethyl-phenyl)-oxazol-4-ylmethoxy]-benzenesulfonyl}2,3-dihydro-1H-indole-2-carboxylic acid described in the patent application WO 03/043985, as compound 19 of Example 4, and GI-262570.

Diseases

The invention also extends to the prophylaxis or treatment of any disease or disorder in which MEK kinase plays a role including, without limitation: oncologic, hematologic, inflammatory, ophthalmologic, neurological, immunologic, cardiovascular, and dermatologic diseases as well as diseases caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further, the invention extends to the administration to a human an effective amount of a MEK inhibitor for treating any such disease or disorder.

Diseases or disorders in which MEK kinase plays a role, either directly or via pro-inflammatory cytokines including the cytokines TNF, IL-1, IL-6 and IL-8, include, without limitation: dry eye, glaucoma, autoimmune diseases, inflammatory diseases, destructive-bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation, and conditions associated with prostaglandin endoperoxidase synthetase-2 (COX-2).

In certain aspects of the invention, the disease is a hyperproliferative condition of the human or animal body, including, but not limited to cancer, hyperplasias, restenosis, inflammation, immune disorders, cardiac hypertrophy, atherosclerosis, pain, migraine, angiogenesis-related conditions or disorders, proliferation induced after medical conditions, including but not limited to surgery, angioplasty, or other conditions.

In further embodiments, said hyperproliferative condition is selected from the group consisting of hematologic and nonhematologic cancers. In yet further embodiments, said hematologic cancer is selected from the group consisting of multiple myeloma, leukemias, and lymphomas. In yet further embodiments, said leukemia is selected from the group consisting of acute and chronic leukemias. In yet further embodiments, said acute leukemia is selected from the group consisting of acute lymphocytic leukemia (ALL) and acute nonlymphocytic leukemia (ANLL). In yet further embodiments, said chronic leukemia is selected from the group consisting of chronic lymphocytic leukemia (CLL) and chronic myelogenous leukemia (CML). In further embodiments, said lymphoma is selected from the group consisting of Hodgkin's lymphoma and non-Hodgkin's lymphoma. In further embodiments, said hematologic cancer is multiple myeloma. In other embodiments, said hematologic cancer is of low, intermediate, or high grade. In other embodiments, said non-hematologic cancer is selected from the group consisting of: brain cancer, cancers of the head and neck, lung cancer, breast cancer, cancers of the reproductive system, cancers of the digestive system, pancreatic cancer, and cancers of the urinary system. In further embodiments, said cancer of the digestive system is a cancer of the upper digestive tract or colorectal cancer. In further embodiments, said cancer of the urinary system is bladder cancer or renal cell carcinoma. In further embodiments, said cancer of the reproductive system is prostate cancer.

Additional types of cancers which may be treated using the compounds and methods described herein include: cancers of oral cavity and pharynx, cancers of the respiratory system, cancers of bones and joints, cancers of soft tissue, skin cancers, cancers of the genital system, cancers of the eye and orbit, cancers of the nervous system, cancers of the lymphatic system, and cancers of the endocrine system. In certain embodiments, these cancer s may be selected from the group consisting of: cancer of the tongue, mouth, pharynx, or other oral cavity; esophageal cancer, stomach cancer, or cancer of the small intestine; colon cancer or rectal, anal, or anorectal cancer; cancer of the liver, intrahepatic bile duct, gallbladder, pancreas, or other biliary or digestive organs; laryngeal, bronchial, and other cancers of the respiratory organs; heart cancer, melanoma, basal cell carcinoma, squamous cell carcinoma, other non-epithelial skin cancer; uterine or cervical cancer; uterine corpus cancer; ovarian, vulvar, vaginal, or other female genital cancer; prostate, testicular, penile or other male genital cancer; urinary bladder cancer; cancer of the kidney; renal, pelvic, or urethral cancer or other cancer of the genito-urinary organs; thyroid cancer or other endocrine cancer; chronic lymphocytic leukemia; and cutaneous T-cell lymphoma, both granulocytic and monocytic.

Yet other types of cancers which may be treated using the compounds and methods described herein include: adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, hemangioblastoma, hepatocellular carcinoma, hepatoma, Kaposi's sarcoma, large cell carcinoma, leiomyosarcoma, liposarcoma, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, and Wilm's tumor.

The disease to be treated using the compounds, compositions and methods described herein may be a hematologic disorder. In certain embodiments, said hematologic disorder is selected from the group consisting of sickle cell anemia, myelodysplastic disorders (MDS), and myeloproliferative disorders. In further embodiments, said myeloproliferative disorder is selected from the group consisting of polycythemia vera, myelofibrosis and essential thrombocythemia.

The compounds, compositions and methods described herein may be useful as anti-inflammatory agents with the additional benefit of having significantly less harmful side effects. The compounds, compositions and methods described herein are useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. The compounds, compositions and methods described herein are also useful in treating osteoporosis and other related bone disorders. These compounds, compositions and methods described herein can also be used to treat gastrointestinal conditions such as reflux esophagitis, diarrhea, inflammatory bowel disease, Crohn's disease, gastritis, irritable bowel syndrome and ulcerative colitis. The compounds, compositions and methods described herein may also be used in the treatment of pulmonary inflammation, such as that associated with viral infections and cystic fibrosis. In addition, the compounds, compositions and methods described herein are also useful in organ transplant patients either alone or in combination with conventional immunomodulators. Yet further, the compounds, compositions and methods described herein are useful in the treatment of pruritis and vitaligo. In particular, compounds, compositions and methods described herein are useful in treating the particular inflammatory disease rheumatoid arthritis.

Further inflammatory diseases which may be prevented or treated include, without limitation: asthma, allergies, respiratory distress syndrome or acute or chronic pancreatitis. Furthermore, respiratory system diseases may be prevented or treated including but not limited to chronic obstructive pulmonary disease, and pulmonary fibrosis. In addition, MEK kinase inhibitors described herein are also associated with prostaglandin endoperoxidase synthetase-2 (COX-2) production. Pro-inflammatory mediators of the cyclooxygenase pathway derived from arachidonic acid, such as prostaglandins, are produced by inducible COX-2 enzyme. Regulation of COX-2 would regulate these pro-inflammatory mediators, which affect a wide variety of cells and are important and critical inflammatory mediators of a wide variety of disease states and conditions. In particular, these inflammatory mediators have been implicated in pain, such as in the sensitization of pain receptors, and edema. Accordingly, additional MEK kinase-mediated conditions which may be prevented or treated include edema, analgesia, fever and pain such as neuromuscular pain, headache, dental pain, arthritis pain and pain caused by cancer.

Further, the disease to be treated by the compounds, compositions and methods described herein may be an ophthalmologic disorder. Ophthalmologic diseases and other diseases in which angiogenesis plays a role in pathogenesis, may be treated or prevented and include, without limitation, dry eye (including Sjogren's syndrome), macular degeneration, closed and wide angle glaucoma, retinal ganglion degeneration, occular ischemia, retinitis, retinopathies, uveitis, ocular photophobia, and of inflammation and pain associated with acute injury to the eye tissue. The compounds, compositions and methods described herein can be used to treat glaucomatous retinopathy and/or diabetic retinopathy. The compounds, compositions and methods described herein can also be used to treat post-operative inflammation or pain as from ophthalmic surgery such as cataract surgery and refractive surgery. In further embodiments, said ophthalmologic disorder is selected from the group consisting of dry eye, closed angle glaucoma and wide angle glaucoma.

Further, the disease to be treated by the compounds, compositions and methods described herein may be an autoimmune disease. Autoimmune diseases which may be prevented or treated include, but are not limited to: rheumatoid arthritis, inflammatory bowel disease, inflammatory pain, ulcerative colitis, Crohn's disease, periodontal disease, temporomandibular joint disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs. host disease, and psoriasis. Inflammatory diseases which may be prevented or treated include, but are not limited to: asthma, allergies, respiratory distress syndrome or acute or chronic pancreatitis. In particular, compounds, compositions and methods described herein are useful in treating the particular autoimmune disease rheumatoid arthritis.

Further, the disease to be treated by the compounds, compositions and methods described herein may be a dermatologic disorder. In certain embodiments, said dermatologic disorder is selected from the group including, without limitation, melanoma, basel cell carcinoma, squamous cell carcinoma, and other non-epithelial skin cancer as well as psoriasis and persistent itch, and other diseases related to skin and skin structure, may be treated or prevented with MEK kinase inhibitors of this invention.

Metabolic diseases which may be treated or prevented include, without limitation, metabolic syndrome, insulin resistance, and Type 1 and Type 2 diabetes. In addition, the compositions described herein can be used to treat insulin resistance and other metabolic disorders such as atherosclerosis that are typically associated with an exaggerated inflammatory signaling.

The compounds, compositions and methods described herein are also useful in treating tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, hypersensitivity, swelling occurring after injury, ischemias including myocardial ischemia, cardiovascular ischemia, and ischemia secondary to cardiac arrest, and the like. The compounds, compositions and methods described herein can also be used to treat allergic rhinitis, respiratory distress syndrome, endotoxin shock syndrome, and atherosclerosis.

Further, the disease to be treated by the compounds, compositions and methods described herein may be a cardiovascular condition. In certain embodiments, said cardiovascular condition is selected from the group consisting of atherosclerosis, cardiac hypertrophy, idiopathic cardiomyopathies, heart failure, angiogenesis-related conditions or disorders, and proliferation induced after medical conditions, including, but not limited to restenosis resulting from surgery and angioplasty.

Further, the disease to be treated by the compounds, compositions and methods described herein may be a neurological disorder. In certain embodiments, said neurologic disorder is selected from the group consisting of Parkinson's disease, Alzheimer's disease, Alzheimer's dementia, and central nervous system damage resulting from stroke, ischemia and trauma. In other embodiments, said neurological disorder is selected from the group consisting of epilepsy, neuropathic pain, depression and bipolar disorders.

Kits

The compounds, compositions and methods described herein provide kits for the treatment of disorders, such as the ones described herein. These kits comprise a compound, compounds or compositions described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

Besides being useful for human treatment, the compounds and formulations of the present invention are also useful for veterinary treatment of companion animals, exotic animals and farm animals, including mammals, rodents, and the like. More preferred animals include horses, dogs, and cats.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

I Chemical Syntheses

Example 1

(2-fluoro-4-iodo-phenyl)-(2,3,5-trifluoro-6-nitrophenyl)-amine

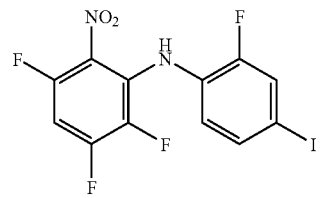

A stirred solution of 2-fluoro-4-iodoaniline (3.64 gm, 15.37 mmol) in dry THF (100 ml) under nitrogen was cooled to −78° C. and a solution of 1.0 M lithium hexamethyl disilazide (LiN(SiMe$_3$)$_2$) "LHMDS" (15.37 ml, 15.37 mmol) was added slowly. This reaction mixture was stirred at −78° C. for another hour, and then 2,3,4,6-tetrafluoronitrobenzene was added. The reaction mixture was allowed to warm to room temperature, and stirring continued for another 16 hours. Ethyl acetate (200 mL) was added to the reaction mixture, and the mixture was washed with water. The organic layer was dried over sodium sulfate and further purified by column chromatography to provide yellow solid (3.75 gm, yield: 59.24%).

M-H+: 410.9

$^1$H NMR (DMSO, 300 MHz): 6.85 (t, 1H); 7.38 (d, 1H); 7.62 (m, 2H); 8.78 (s, 1H)

Example 2

(2,3-Difluoro-5-methoxy-6-nitro-phenyl)-(2-fluoro-4-iodo-phenyl)-amine

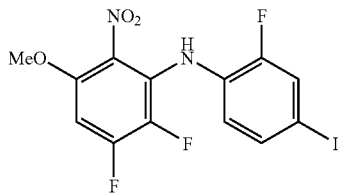

A stirred solution of (2-fluoro-4-iodo-phenyl)-(2,3,5-trifluoro-6-nitro-phenyl)-amine (1.23 gm, 3 mmol) in dry THF (25 ml) was cooled to −78° C. under nitrogen, and a solution of 25% sodium methoxide (0.68 ml, 0.3 mmol) was added slowly. The reaction mixture was allowed to warm to room temperature, and stirring was continued for another 16 hours. TLC indicated incomplete reaction. Ethyl acetate (100 ml) was added to the reaction mixture, and the mixture was washed with water. The organic layer was dried over sodium sulfate and further purified by column chromatography to provide a yellow solid (0.6 gm, yield: 47.6%).

Example 3

5,6-difluoro-N1-(2-fluoro-4-iodophenyl)-3-methoxy-benzene-1,2-diamine

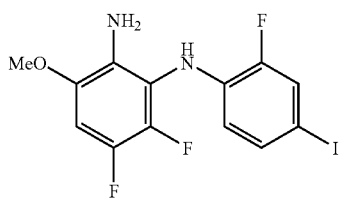

To a stirred solution of (2,3-difluoro-5-methoxy-6-nitro-phenyl)-(2-fluoro-4-iodo-phenyl)-amine (0.57 gm, 1.34 mmol) ethanol (20 ml), ammonium chloride (1.18 gm, 20.16 mmol) and iron powder (1.15 gm, 21.44 mmol) were added. This reaction mixture was kept stirring at reflux for 16 hours. The reaction mixture was allowed to cool and was filtered over celite and concentrated to dryness. The residue obtained was taken into ethyl acetate and was washed with water. The organic layer was dried over sodium sulfate and further purified by crystallization from ethanol to provide an off-white solid (0.47 gm, yield: 90.3%).

M-H+: 393.2

$^1$H NMR (DMSO, 300 MHz): 3.76 (s, 3H); 6.1 (t, 1H); 6.8-7.0 (r, 1H); 7.2 (d, 1H); 7.35 (s, 1H); 7.42 (d, 1H)

Example 4

(2,2-dimethyl-1,3-dioxolan-4-yl)methan sulfonamidyl chloride

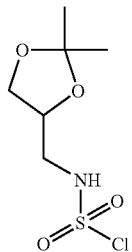

Sulfuryl chloride (90 µL, 1.12 mmol) in dry dichloromethane (5 mL) was cooled to −78° C. in an acetone/dry-ice bath under argon. A solution of (2,2-dimethyl-1,3-dioxolan-4-yl)methanamine, (145 µL, 1.12 mmol) and DMAP (138 mg, 1.13 mmol) in dry DCM (2 mL) was added dropwise through a syringe to the solution over 10 min. The resulting mixture was maintained at −50° C. for 1 hr; then the bath was removed, and stirring was continued for 2 hrs. The crude reaction product was used for the next reaction without workup.

Example 5

2-(2,2-Dimethyl-[1,3]dioxolan-4-yl)-methane-amino-sulfonic acid [3,4-difluoro-2-(2-fluoro-4-iodo-phenylamino)-6-methoxyl-phenyl]-amide

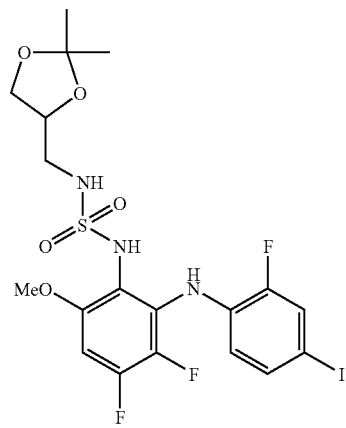

The crude reaction mixture of (2,2-dimethyl-1,3-dioxolan-4-yl)methan sulfonamidyl chloride, prepared in example 4 (1.0 mL, 0.156 mmol, 2.0 eq) was added dropwise to a solution of 5,6-difluoro-N1-(2-fluoro-4-iodophenyl)-3-methoxy-benzene-1,2-diamine (see example 3, 32.6 mg, 0.083 mmol), in dry pyridine (2 mL), at −10° C. The mixture was allowed to warm to room temperature and stirred at room temperature for a further 16 hrs. Water was added, and the mixture was washed with HCl (1N) and extracted with ethyl acetate. The organic layers were combined, dried over MgSO$_4$, and concentrated to give the title compound as a tan paste which was used without further purification in the next reaction step.

MW m/e+Q1 588.4 (MW+1), 610.2 (M+Na); −Q1586.1 (MW−1))

Example 6

3-((2-(2-fluoro-4-iodophenylamino)-3,4-difluoro-6-methoxyphenyl)sulfamidyl)propane-1,2-diol

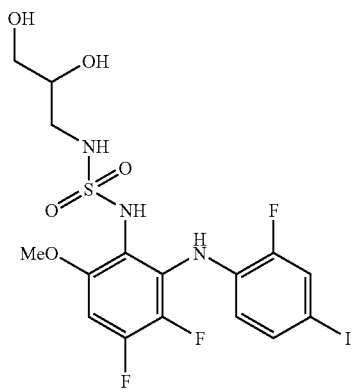

HCl in absolute ethanol (1 mL of 5.3 M) was added to a solution of crude product isolated in example 5 (70 mg) in ethyl acetate (2 mL) and methanol (2 mL) at −5° C. The resulting solution was warmed to room temperature and stirred for 1.5 hrs. Volatiles were removed by rotary evaporation and the final product purified by HPLC (14 mg, 31% overall yield).

MW m/e+Q1 548.3 (MW+1, low intensity), 570.2 (MW+Na)−Q1 546.2 (MW−1)

$^1$H NMR (300 Hz, DMSO-d$_6$) δ ppm 8.75 (s, 1H), 7.53-7.57 (dd, J1=10.8 Hz, J2=1.8 Hz, 1H), 7.47 (s, 1H), 7.32 (d, J=8.4 Hz, 1H), 7.01-7.08 (dd, J1=12.9 Hz, J2=7.5 Hz, 1H), 6.97 (t, J=6.0 Hz, 1H), 3.78 (s, 3H), 3.46 (q, J=6.3 Hz, 2H), 3.00-3.06 (m, 1H), 2.84-2.88 (m, 1H)

Example 7

2-(2,2-Dimethyl-[1,3]dioxolan-4-yl)-methane-amino-sulfonic acid [3,4-difluoro-2-(2-fluoro-4-iodo-phenylamino)-phenyl]-amide

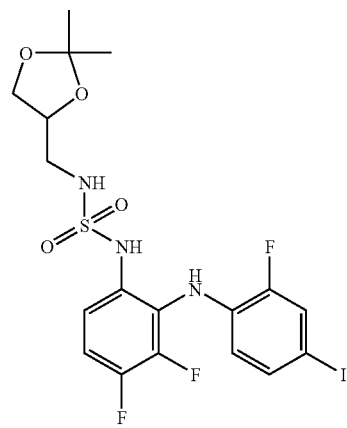

The title compound was synthesized according to the procedures described above and HPLC purified.

Example 8

3,4-Dihydroxy-propane-1-amino-sulfonic acid [3,4-difluoro-2-(2-fluoro-4-iodo-phenylamino)-phenyl]-amide

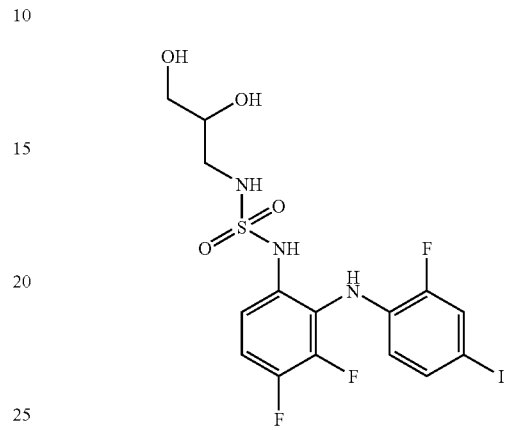

The title compound was synthesized according to the procedures described above and HPLC purified. HPLC purity: 99.2%, retention time=17.0 min.

MW m/z: 516.1 (MW−1).

$^1$H NMR (300 Hz, DMSO-d6) δ ppm 9.05 (s, 1H), 7.57 (t, 1H), 7.37 (t, 1H), 7.20-7.30 (m, 1H), 6.38 (tt, 1H), 4.65 (s, br, 1H), 4.45 (s, br, 1H), 3.46 (m, 2H), 3.20 (in, 1H), 2.94 (m, 1H), 2.80 (m, 1H).

II Biological Activity

Example 9

Generation of IC$_{50}$ Data

Materials and preparation of reagents: Human GST-MEK1 and the constitutively active allele GST-MEK1$^{CA}$ (harboring the mutations Ser218Asp and Ser222Asp) were subcloned into the yeast expression vector pGEM4Z (Promega, Madison, Wis.) from the wild type human MEK1 cDNA. GST-MEK1$^{CA}$ was expressed in *Escherichia coli* and partially purified using Glutathione Sepharose 4B affinity resin (Amersham Pharmacia Biotech, Piscataway, N.J.). The ERK2 allele was subcloned from MAPK2/Erk2 cDNA (wild type) in pUSEamp (Upstate Biotechnology, Inc., Waltham, Mass.) into the vector pET21a (Novagen, Madison, Wis.) resulting in an N-terminal histidine-tagged mouse ERK2 allele. ERK2 was expressed and purified to homogeneity [Zhang, 1993 #33]. Myelin basic protein (MBP) was purchased from Gibco BRL (Rockville, Md.). EasyTides adenosine 5'-triphosphate (ATP) ([γ-$^{33}$P]) (NEN Perkin Elmer, Wellesley, Mass.) was the source of radiolabel for all kinase reactions. Activated Raf-1 (truncated) and activated MAPKinase 2/ERK2 were purchased from Upstate, Inc. (Lake Placid, N.Y.). 4-20% Criterion Precast gels were purchased from Bio-Rad (Hercules, Calif.).

Example 10

Generation of EC$_{50}$ Data

Determination of enzymatic activity: Compounds were diluted from dimethylsulfoxide (DMSO) stocks into 1×HMNDE (20 mM HEPES pH 7.2, 1 mM MgCl$_2$, 100 mM NaCl, 1.25 mM DTT, 0.2 mM EDTA). A typical 25-microliter assay contained 0.002 nanomoles MEK1$^{CA}$, 0.02 nanomoles ERK2, 0.25 nanomoles MBP, 0.25 nanomoles unlabeled ATP, and 0.1 µCi [γ$^{33}$P] ATP. The screening assay essentially comprised four additions. Five µl of diluted compound were dispensed to 96-well assay plates. Ten µl of 2.5× enzyme cocktail (MEK1$^{CA}$ and ERK2 only) were then added to each well followed by a pre-incubation for 30 minutes at ambient temperature. Ten µl of 2.5× substrate cocktail (labeled and unlabeled ATP plus MBP) were then added, followed by incubation for 60 minutes at ambient temperature. Finally, 100 µl of 10% trichloroacetic acid (TCA) were added and incubated for 30 minutes at room temperature to halt the reaction and precipitate radiolabeled protein products. Reaction products were harvested on glass fiber 96 well filter plates prewetted with water and 1% pyrophosphate. The filter plate was then washed 5 times with water. Water was displaced by absolute ethanol and the plate was allowed to air dry for 30 minutes at room temperature. A back seal was applied manually and 40 µl of scintillation cocktail were dispensed to each well. A top seal was applied and the plate was counted in the TopCount for two seconds per well. For certain experiments a truncated version of MEK that requires activation by Raf kinase were used.

Example 11

Growth Inhibition Assay (GI$_{50}$)

For growth inhibition experiments, A375 cells were plated in white 384-well microplates at 1000 cells/20 ml/well. After 24 hr, 5 ml of a 5× drug stock solution was added. All drugs were initially prepared as 200× stocks in DMSO, such that final DMSO concentration was 0.5%. Cells were incubated for 48 hr at 37° C. and ATP levels were determined using CellTiterGlo (Promega, Madison, Wis.). A control MEK inhibitor was used to determine the ATP level corresponding to full growth inhibition and the concentration of test compound that gave ATP levels midway between full growth inhibition and vehicle only ATP levels was determined to be the GI$_{50}$ using non-linear regression (GraphPad Prism 4).

Example 12

The MEK IC$_{50}$ of the compound prepared in example 6, was determined per the procedures outlined in examples 9 and 10, with the results shown below:

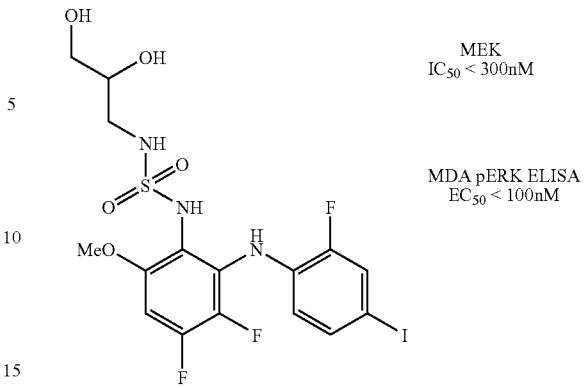

Example 13

The MEK activity of the compound prepared in example 8, was determined per the procedures outlined in examples 9, 10 and 11, with the results shown below:

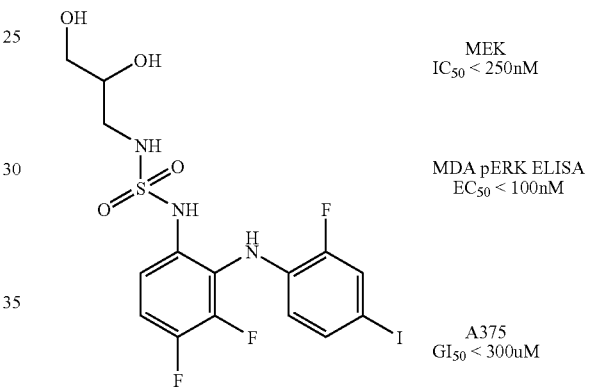

What is claimed is:

1. A compound of formula I or a pharmaceutically acceptable salt thereof

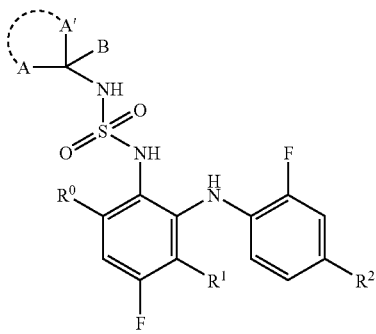

formula I wherein

B is H, C$_1$-C$_4$ alkyl, or C$_2$-C$_6$ alkenyl;
  wherein said C$_1$-C$_4$ alkyl is optionally substituted with one or two hydroxy groups;

A and A' are each independently H, C$_1$-C$_4$ alkyl, or C$_2$-C$_6$ alkenyl;
  wherein each C$_1$-C$_4$ alkyl is independently optionally substituted with one or two hydroxy groups; or A and A' together with the carbon atom to which they are attached, form a cyclopropyl, cyclobutyl, or cyclopentyl group, optionally substituted with at least one methyl, hydroxy, or halogen;

$R^1$ is H or F;

$R^2$ is Br or I;

$R^0$ is $OR^3$;

wherein $R^3$ is H, $C_1$-$C_4$ alkyl or phenyl;

wherein each $C_1$-$C_4$ alkyl or phenyl group is independently optionally substituted with at least one halogen, hydroxy, azido, cyano, cyanomethyl, nitro, phenyl, difluoromethyl, trifluoromethyl, methoxy, or $C_1$-$C_4$ alkoxy.

2. The compound of claim 1, wherein $R^0$ is $OR^3$; and $R^3$ is $C_1$-$C_4$ alkyl optionally substituted with at least one halogen, methyl, trifluoromethyl, hydroxy, or alkoxy.

3. The compound of claim 1, wherein

B is —H, —CH$_3$, —CH$_2$CH$_2$OH, —CH$_2$CH(OH)CH$_2$OH, —(CH$_2$)$_2$CH(OH)CH$_2$OH, —CH$_2$—CH=CH$_2$ or —CH$_2$—CH$_2$CH=CH$_2$; and A and A' are both H; or A and A' together with the carbon atom to which they are attached are

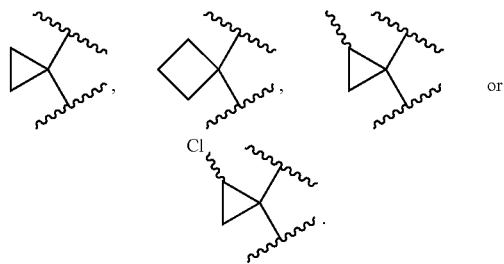

.

4. A pharmaceutical composition comprising a pharmaceutically acceptable carrier and a compound of formula I or a pharmaceutically acceptable salt thereof;

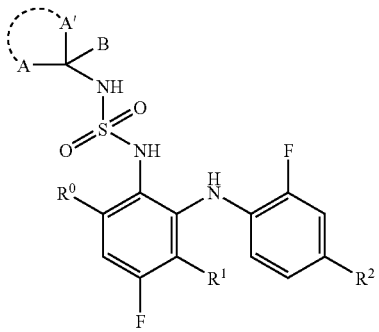

formula I wherein

B is H, $C_1$-$C_4$ alkyl, or $C_2$-$C_6$ alkenyl;

wherein said $C_1$-$C_4$ alkyl is optionally substituted with one or two hydroxy groups;

A and A' are each independently H, $C_1$-$C_4$ alkyl, or $C_2$-$C_6$ alkenyl;

wherein each $C_1$-$C_4$ alkyl is independently optionally substituted with one or two hydroxy groups; or A and A' together with the carbon atom to which they are attached, form a cyclopropyl, cyclobutyl, or cyclopentyl group, optionally substituted with at least one methyl, hydroxy, or halogen;

$R^1$ is H or F;

$R^2$ is Br or I;

$R^0$ is $OR^3$;

wherein $R^3$ is H, $C_1$-$C_4$ alkyl or phenyl;

wherein each $C_1$-$C_4$ alkyl or phenyl group is independently optionally substituted with at least one halogen, hydroxy, azido, cyano, cyanomethyl, nitro, phenyl, difluoromethyl, trifluoromethyl, methoxy, or $C_1$-$C_4$ alkoxy.

5. A compound of formula I

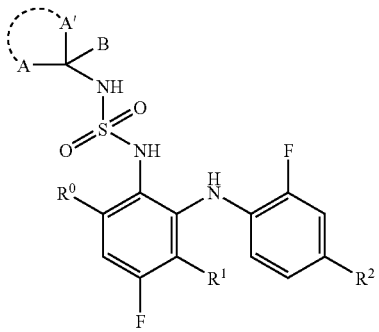

formula I wherein the compound is as recited in the following table:

| CPD # | —C(A)A'— | —B | $R^0$ | $R^1$ | $R^2$ |
|---|---|---|---|---|---|
| 1 | —CH$_2$— | —H | OCH$_3$ | F | I |
| 2 | —CH$_2$— | —CH$_2$CH(OH)CH$_2$OH | OCH$_3$ | F | I |
| 3 | 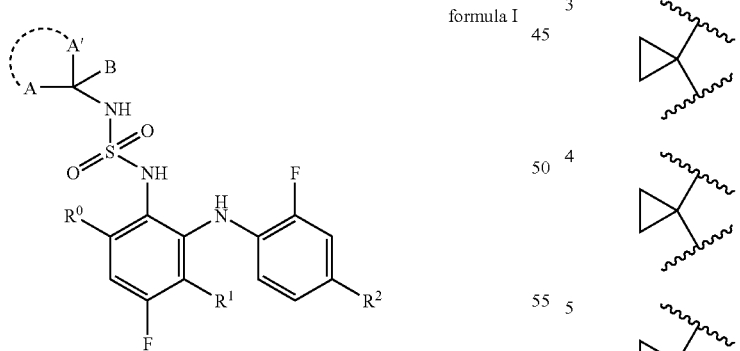 | —CH$_2$—CH$_2$—CH=CH$_2$ | OCH$_3$ | F | I |
| 4 | | —CH$_3$ | OCH$_3$ | F | I |
| 5 | | —CH$_2$CH$_2$OH | OCH$_3$ | F | I |
| 6 | | —(CH$_2$)$_2$CH(OH)CH$_2$OH | OCH$_3$ | F | I |

-continued

| CPD # | —C(A)A'— | —B | R⁰ | R¹ | R² |
|---|---|---|---|---|---|
| 7 | (cyclopropyl with H, CH₃) | —(CH₂)₂CH(OH)CH₂OH | OCH₃ | F | I |
| 8 | (spirocyclopropyl) | —(CH₂)₂CH(OH)CH₂OH | OCH₃ | F | I |
| 9 | (spirocyclopropyl with Cl) | —CH₂CH(OH)CH₂OH | OCH₃ | F | I |
| 10 | (spirocyclopropyl with Cl) | —H | OCH₃ | F | I |
| 11 | (spirocyclopropyl) | —CH₂CH(OH)CH₂OH | OCH₃ | F | I |
| 12 | (spirocyclopropyl) | —CH₂—CH₂—CH=CH₂ | OCH₃ | F | I |
| 13 | (spirocyclopropyl with Cl) | —CH₂CH₂OH | OCH₃ | F | I |
| 14 | (spirocyclopentyl with Cl) | —CH₃ | OCH₃ | F | I |
| 15 | —CH₂— | —H | OCH₃ | H | I |
| 16 | —CH₂— | —CH₂CH(OH)CH₂OH | OCH₃ | H | Br |
| 17 | (spirocyclopropyl) | —CH₂—CH₂—CH=CH₂ | OCH₃ | H | I |
| 18 | (spirocyclopropyl) | —CH₃ | OCH₃ | H | Br |
| 19 | (spirocyclopropyl) | —CH₂CH₂OH | OCH₃ | H | Br |
| 20 | (spirocyclopropyl) | —(CH₂)₂CH(OH)CH₂OH | OCH₃ | H | Br |
| 21 | (cyclopropyl with H, CH₃) | —(CH₂)₂CH(OH)CH₂OH | OCH₃ | H | Br | or a pharmaceutically acceptable salt thereof.

6. A pharmaceutical composition comprising a pharmaceutically acceptable carrier and a compound of claim 5 or a pharmaceutically acceptable salt thereof.

7. The compound of claim 2, wherein

B is —H, —CH₃, —CH₂CH₂OH, —CH₂CH(OH)CH₂OH, —(CH₂)₂CH(OH)CH₂OH, —CH₂—CH=CH₂ or —CH₂—CH₂CH=CH₂; and A and A' are both H; or A and A' together with the carbon atom to which they are attached are (spirocyclopropyl), (spirocyclobutyl), or (spirocyclopropyl with Cl).

8. The compound of claim 1, wherein

B is —H, —CH₃, —CH₂CH₂OH, —CH₂CH(OH)CH₂OH, —(CH₂)₂CH(OH)CH₂OH, —CH₂—CH=CH₂ or —CH₂—CH₂CH=CH₂.

9. The compound of claim 1, wherein

A and A' are both H.

10. The compound of claim 1, wherein

A and A' together with the carbon atom to which they are attached are (spirocyclopropyl), (spirocyclobutyl), or -continued

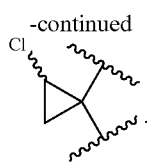

11. The compound of claim 1, wherein $R^3$ is methyl.
12. The compound of claim 7, wherein $R^3$ is methyl.
13. The compound of claim 8, wherein $R^3$ is methyl.
14. The compound of claim 9, wherein $R^3$ is methyl.
15. The compound of claim 10, wherein $R^3$ is methyl.
16. A compound according to claim 5, which is of formula I

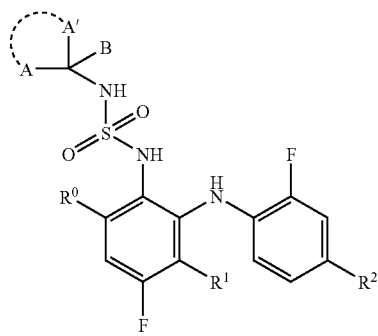

formula I wherein the compound is as recited in the following table:

| CPD# | —C(A)A'— | —B | $R^0$ | $R^1$ | $R^2$ |
|---|---|---|---|---|---|
| 1 | —CH$_2$— | —H | OCH$_3$ | F | I |
| 2 | —CH$_2$— | —CH$_2$CH(OH)CH$_2$OH | OCH$_3$ | F | I |

-continued

| CPD# | —C(A)A'— | —B | $R^0$ | $R^1$ | $R^2$ |
|---|---|---|---|---|---|
| 15 | —CH$_2$— | —H | OCH$_3$ | H | I |
| 16 | —CH$_2$— | —CH$_2$CH(OH)CH$_2$OH | OCH$_3$ | H | Br | or a pharmaceutically acceptable salt thereof.

17. A compound according to claim 5, which is of formula I

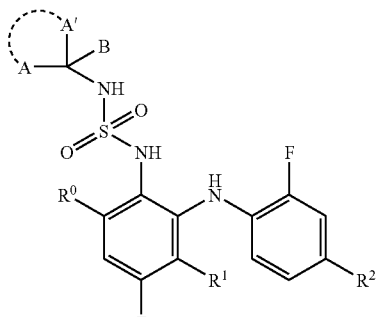

formula I wherein the compound is as recited in the following table:

| CPD# | —C(A)A'— | —B | $R^0$ | $R^1$ | $R^2$ |
|---|---|---|---|---|---|
| 2 | —CH$_2$— | —CH$_2$CH(OH)CH$_2$OH | OCH$_3$ | F | I | or a pharmaceutically acceptable salt thereof.

* * * * *

UNITED STATES PATENT AND TRADEMARK OFFICE
CERTIFICATE OF CORRECTION

PATENT NO. : 7,842,836 B2
APPLICATION NO. : 11/734234
DATED : November 30, 2010
INVENTOR(S) : Yan et al.

Page 1 of 1

It is certified that error appears in the above-identified patent and that said Letters Patent is hereby corrected as shown below:

Column 95, line 47 reads "   " should read 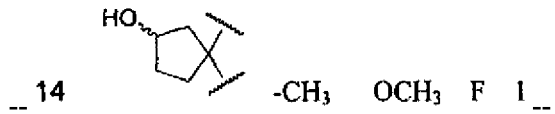

Signed and Sealed this
Fifteenth Day of March, 2011

David J. Kappos
*Director of the United States Patent and Trademark Office*